(12) United States Patent
Teyton et al.

(10) Patent No.: US 8,932,594 B2
(45) Date of Patent: Jan. 13, 2015

(54) ADJUVANTS AND METHODS OF USE

(75) Inventors: Luc Teyton, Del Mar, CA (US); Albert Bendelac, Chicago, IL (US); Paul B. Savage, Mapleton, UT (US)

(73) Assignees: The Scripps Research Institute, La Jolla, CA (US); The University of Chicago, Chicago, IL (US); Brigham Young University, Provo, UT (US)

( * ) Notice: Subject to any disclaimer, the term of this patent is extended or adjusted under 35 U.S.C. 154(b) by 659 days.

(21) Appl. No.: 12/850,428

(22) Filed: Aug. 4, 2010

(65) Prior Publication Data

US 2011/0027323 A1 Feb. 3, 2011

Related U.S. Application Data

(62) Division of application No. 11/771,128, filed on Jun. 29, 2007, now Pat. No. 7,794,722.

(60) Provisional application No. 60/806,330, filed on Jun. 30, 2006.

(51) Int. Cl.

| A61K 39/00 | (2006.01) |
|---|---|
| A61K 39/38 | (2006.01) |
| A61K 45/00 | (2006.01) |
| A61K 47/00 | (2006.01) |
| A61K 31/70 | (2006.01) |
| A01N 43/04 | (2006.01) |
| A61K 31/7032 | (2006.01) |
| A61K 47/48 | (2006.01) |

(52) U.S. Cl.
CPC ....... *A61K 31/7032* (2013.01); *A61K 47/48046* (2013.01); *A61K 47/48092* (2013.01)
USPC ................ 424/184.1; 424/278.1; 514/25

(58) Field of Classification Search
USPC ................ 424/184.1, 278.1; 514/25
See application file for complete search history.

(56) References Cited

U.S. PATENT DOCUMENTS

| 4,952,683 A | 8/1990 | Tschannen et al. |
|---|---|---|
| 5,010,059 A | 4/1991 | Schmidt et al. |
| 5,242,800 A | 9/1993 | Jimenez et al. |
| 5,604,207 A | 2/1997 | DeFrees et al. |
| 5,767,092 A | 6/1998 | Koezuka et al. |
| 5,780,441 A | 7/1998 | Higa et al. |
| 5,849,716 A | 12/1998 | Akimoto et al. |
| 5,936,076 A | 8/1999 | Higa et al. |
| 6,071,884 A | 6/2000 | Koezuka et al. |
| 6,531,453 B1 | 3/2003 | Taniguchi et al. |
| 6,747,010 B2 | 6/2004 | Taniguchi et al. |
| 7,273,852 B2 | 9/2007 | Tsuji et al. |
| 7,794,722 B2 | 9/2010 | Teyton et al. |
| 2002/0115624 A1 | 8/2002 | Behar et al. |
| 2003/0153514 A1 | 8/2003 | Yagita |
| 2003/0157135 A1 | 8/2003 | Tsuji et al. |
| 2004/0127429 A1 | 7/2004 | Tsuji |
| 2004/0266726 A1 | 12/2004 | Yagita |
| 2006/0073118 A1 | 4/2006 | Bendelac et al. |
| 2006/0211856 A1 | 9/2006 | Tsuji et al. |
| 2006/0264382 A1 | 11/2006 | Savage et al. |
| 2008/0279894 A1 | 11/2008 | Savage et al. |

FOREIGN PATENT DOCUMENTS

| EP | 0 717 995 A2 | 6/1996 |
|---|---|---|
| EP | 1 437 358 A1 | 7/2004 |
| EP | 1 452 181 A1 | 9/2004 |
| JP | 2008-533762 | 8/2008 |
| WO | WO 92/19633 | 11/1992 |
| WO | WO 03/018039 | 3/2003 |
| WO | WO 2004/094444 | 11/2004 |
| WO | WO 2005/000348 | 1/2005 |
| WO | WO 2005/032462 A2 | 4/2005 |
| WO | WO 2005/046637 A2 | 5/2005 |
| WO | WO 2005/120574 A1 | 12/2005 |
| WO | WO 2006/026389 A2 | 3/2006 |
| WO | WO 2006/083671 | 8/2006 |
| WO | WO 2007/074788 A1 | 5/2007 |
| WO | WO 2007/118234 | 10/2007 |
| WO | WO 2008/005824 | 1/2008 |

OTHER PUBLICATIONS

Minor, P.D. Problems in the development of new vaccines. Microbiology Today, vol. 27, p. 74-75.*
"Immunotherapy" from the American Cancer Society [online] Retrieved on May 28, 2013. Retrieved from the internet at <http://www.cancer.org/treatment/treatmentsandsideeffects/treatment-types/immunotherapy/immunotherapy-cancer-vaccines>.*
Minor, P.D. (2000) Problems in the development of new vaccines. Microbiology Today, vol. 27, p. 74-75.*
European Search Report mailed Jul. 12, 2012.
Dumoulin, F. et al., "Self-Organizing Properties of Natural and Related Synthetic Glycolipids," *J. Am. Chem. Soc.*, vol. 124, No. 46, pp. 13737-13748 (2002).
Inagaki, M. et al., "Constituents of Crinoidea, 4. Isolation and Structure of Ceramides and Glucocerebrosides from the Feather Star *Comanthus japonica*," *Chem. Pharm. Bull*, vol. 52, No. 1, pp. 1307-1311 (Nov. 2004).
Kang, S. et al., "Cyclooxygenase-2 Inhibitory Cerebrosides from Phytolaccae Radix," *Chem. Pharm. Bull.*, vol. 49, No. 3, pp. 321-323 (2001).
Kobayashi, E. et al., "Enhancing Effects of α-, β-Monoglycosylceramides on Natural Killer Cell Activity," *Bioorganic & Medicinal Chemistry*, vol. 4, No. 4, pp. 615-619 (1996).
Margalit, M. et al., "715 β-Glycolipid-induced suppression of hepatocellular carcinoma is associated with increased intrahepatic NKT lymphocytes and increased expression of stat1," *Journal of Hepatology, Munksgaard International Publishers*, Copenhagen, Denmark, vol. 42, p. 260 (Apr. 1, 2005).
Motoki, K. et al., "Antitumor activities of α-, β-monogalactosylceramides and four diastereomers of an α-galactosylceramide," *Bioorganic & Medicinal Chemistry Letters*, vol. 5, No. 7, pp. 705-710 (1995).

(Continued)

*Primary Examiner* — Scarlett Goon
(74) *Attorney, Agent, or Firm* — Merchant & Gould P.C.

(57) ABSTRACT

Compositions comprising NKT cell agonist compounds and a physiologically acceptable vehicle are provided. Methods of stimulating an NKT cell and enhancing an immune response are also disclosed. Further provided are vaccine preparations comprising NKT cell agonist compounds.

24 Claims, 15 Drawing Sheets

(56) References Cited

OTHER PUBLICATIONS

Osiecki-Newman, K. et al., "Human acid β-glucosidase: use of inhibitors, alternative substrates and amphiphiles to investigate the properties of the normal and Gaucher disease active sites," *Biochimica et Biophysica Acta*, vol. 915, pp. 87-100 (1987).

Parekh, V. et al., Quantitative and Qualitative Differences in the In Vivo Response of NKT Cells to Distinct α- and β-Anomeric Glycolipids, *The Journal of Immunology*, vol. 173, pp. 3693-3706 (2004).

Pettit, G. et al., Antineoplastic Agents. 545. Isolation and Structure of Turbostatins 1-4 from the Asian Marine Mollusk *Turbo stenogyrus*, *J. Nat. Prod.*, vol. 68, pp. 974-978 (2005).

Schmidt, R. et al., "Synthesis of D-*ribo*- and L-*lyxo*-phytophingosine: Transformation into the corresponding lactosylceramides," *Carbohydrate Research*, vol. 174, pp. 169-179 (1988).

Schwarzmann, G. et al., "Demonstration of Direct Glycosylation of Nondegradable Glucosylceramide Analogs in Cultured Cells," *Journal of Biological Chemistry*, vol. 270, No. 36, pp. 21271-21276 (Sep. 8, 1995).

Yamada, K. et al., "Isolation and Structure of Biologically Active Glycosphingolipids from the Sea Cucumber *Cucumaria echinata*," *Eur. J. Org. Chem.*, pp. 371-378 (1998).

Ando, H. et al., "Solid-phase capture-release strategy applied to oligosaccharide synthesis on a soluble polymer support," *Angew. Chem. Int. Ed.*, vol. 40, pp. 4725-4728 (2001).

Bendelac, A. et al., "Increased interleukin 4 and immunoglobulin E production in transgenic mice overexpressing NK1 T cells," *J. Exp. Med.*, vol. 184, pp. 1285-1293 (1996).

Benlagha, K. et al., "In vivo identification of glycolipid antigen-specific T cells using fluorescent CD1d tetramers," *J. Exp. Med.*, vol. 191, pp. 1895-1903 (2000).

Brigl, M. et al., "CD1: T cell function and antigen presentation," *Annu. Rev. Immunol.*, vol. 22, pp. 817-890 (2004).

Brigl, M. et al., "Mechanism of CD1d-restricted natural killer T cell activation during microbial infection," *Nat. Immunol.*, vol. 3, pp. 1230-1237 (2003).

Brutkiewicz, R. et al., "CD1d-mediated antigen presentation to natural killer T (NKT) cells," *Critical Reviews in Immunology*, vol. 23, pp. 403-419 (2003).

Brutkiewicz, R. et al., "Natural killer T (NKT) cells and their role in antitumor immunity," *Critical Reviews in Oncology/Hematology*, vol. 41, pp. 287-298 (2002).

Cantu, C. et al., "The paradox of immune molecular recognition of alpha-galactosylceramide: low affinity, low specificity for CD1d, high affinity for alpha beta TCRs," *J. Immunol*, vol. 170, pp. 4673-4682 (2003).

Corey et al., "A new method for the synthesis of organic nitro compounds," *J. Am. Chem. Soc.*, vol. 106, pp. 3682-3683 (1984).

Dascher, C. et al., "CD1 Antigen Presentation and Infectious Disease," *Contributions to Microbiology*, vol. 10, pp. 164-182 (2003).

Davis, N. et al., "Chemical Synthesis of Disaccharides Which are Partial Structures of the Glycosaminoglycan Heparan Sulfate," *J. Chem. Soc.*, vol. 1, pp. 359-368 (1994).

European Office Action for Application No. 03816701.1 dated Nov. 29, 2007.

Fujii, S. et al., "Activation of natural killer T cells by alpha-galactosylceramide rapidly induces the full maturation of dendritic cells in vivo and thereby acts as an adjuvant for combined CD4 and CD8 T cell immunity to a coadministered protein," *J. Exp. Med.*, vol. 198, pp. 267-279 (2003).

Garrity, G. et al., Taxonomic Outline of the Procaryotic Genera, *Bergey's Manual of Systematic Bacteriology*, 2nd Edition (Apr. 2001).

Godfrey, D. et al., "Going both ways: immune regulation via CD1d-dependent NKT cells," *J. Clin. Invest.*, vol. 114, No. 10, pp. 1379-1388 (2004).

Godfrey, D. et al., "The elusive NKT cell antigen—is the search over?" *Science*, vol. 306, pp. 1687-1688 (2004).

Goff, R. et al., "Effects of lipid chain lengths in alpha-galactosylceramides on cytokine release by natural killer T cells," *J. Am. Chem. Soc.*, vol. 126, pp. 13602-13603 (2004).

*Goodman & Gilman's the Pharmacological Basis of Therapeutics*, editors Joel G. Hardman and Lee E. Limbird, published by the McGraw-Hill Companies, Inc., pp. 54-56 (2001).

Gui, M. et al., "TCR beta chain influences but does not solely control autoreactivity of V alpha 14J28IT cells," *J. Immunol.*, vol. 167, No. 11, pp. 6239-6246 (2001).

Gumperz, J. et al., "Functional distinct subsets of CD1d-restricted natural killer T cells revealed by CD1d tetramer staining," *J. Exp. Med.*, vol. 195, No. 5, pp. 625-636 (2002).

Gupta, R. et al., Adjuvants—a balance between toxicity and adjuvanticity, *Vaccine*, vol. 11, No. 3, pp. 293-306 (1993).

Hashimoto, S. et al., "Glycosylation Using Glucopyranosyl Fluorides and Silicon-Based Catalysts, Solvent Dependency of the Stereoselection," *Tetrahedron Letters*, vol. 25, No. 13, pp. 1379-1382 (1984).

Hayashi, M. et al., "Simple Synthesis of Glycosyl Fluorides," *Chem. Letters*, pp. 1747-1750 (1984).

Hermans, I. et al., "NKT cells enhance CD4+ and CD8+ T cell responses to soluble antigen in vivo through direct interaction dendritic cells," *J. Immunol.*, vol. 171, pp. 5140-5147 (2003).

Iida, N. et al., "A sulfated glucosylceramide from rat kidney," *J. Biol. Chem.*, vol. 264, pp. 5974-5980 (1989).

International Search Report and Written Opinion of International Searching Authority of PCT/US06/002781 dated Dec. 20, 2006.

International Search Report and Written Opinion of International Searching Authority for International Application No. PCT/US07/66250 dated Oct. 15, 2007.

International Search Report and Written Opinion of International Searching Authority of PCT/US2007/072451 dated Nov. 27, 2007.

International Search Report of International Searching Authority of PCT/US03/08530 dated Aug. 3, 2004.

Ismail, N. et al., "Overproduction of TNF-alpha b CD8+ type 1 cells and down-regulation of IFN-γ production by CD4+ Th1 cells contribute to toxic shock-like syndrome in an animal model of fatal monocytotropic ehrlichiosis," *J. Immunol.*, vol. 172, pp. 1786-1800 (2004).

Karadimitris, A. et al., "Human CD1d-glycolipid tetramers generated by in vitro oxidative refolding chromatography," *Proc. Natl. Acad. Sci. USA*, vol. 98, No. 6, pp. 3294-3298 (2001).

Kawano, T. et al., "CD1d-restricted and TCR-mediated activation of Vα14 NKT cells by glycosylceramides," *Science*, vol. 278, pp. 1626-1629 (1997).

Khan, M. et al., "Syntheses and Antiinflammatory Activity of Some 6-aryl-2,3,4,5-tetrahydro-3-pyridaziones," *Indian J. Chem.*, vol. 39B, pp. 614-619 (2000).

Kinjo, Y. et al., "Recognition of bacterial glycosphingolipids by natural killer T cells," *Nature*, vol. 434, pp. 520-525 (2005).

Kronenberg, M. et al., "Toward an understanding of NKT cell biology: progress and paradoxes," *Ann. Rev. Immunol.*, vol. 23, pp. 877-900 (2005).

Lee, P. et al., "Testing the NKT cell hypothesis on human IDDM pathogenesis," *J. Clin. Invest.*, vol. 110, No. 6, pp. 793-800 (2002).

Lei, P. et al., "Synthesis of a 3-deoxy-L-iduronic acid containing heparin pentasaccharide to probe the conformation of the antithrombin III binding sequence," *Bioorg. Med. Chem.*, vol. 6, pp. 1337-1346 (1998).

Liu, Y. e al., "A modified alpha-galactosyl ceramide for staining and stimulating natural killer T cells," *J. Immun. Meth.*, vol. 312, No. 1-2, pp. 34-39 (2006).

Matsuda, J. et al., "Tracking the response of natural killer T cells to a glycolipid antigen using CD1d tetramers," *J. Exp. Med.*, vol. 192, No. 5, pp. 741-753 (2000).

Mattner, J. et al., "Exogenous and endogenous glycolipid antigens activate NKT cells during microbial infections," *Nature*, vol. 434, pp. 525-529 (2005).

Mills, K. et al., "The synthesis of internal standards for the quantitative determination of sphingolipids by tandem mass spectrometry," *Rapid Communications in Mass Spectrometry*, vol. 19, pp. 1739-1748 (2005).

(56) References Cited

OTHER PUBLICATIONS

Miyamoto, K. et al., A Synthetic Glycolipid Prevents Autoimmune Encephalomyelitis by Inducing TH2 Bias of Natural Killer T Cells, Nature, vol. 413, pp. 531-534 (2001).
Morita, M. et al., "Structure-Activity Relationship of α-Galactosylceramides Against B16-Bearing Mice," *J. Med. Chem.*, vol. 38, pp. 2176-2187 (1995).
Nakagawa, R. et al., "Mechanisms of the Antimetastatic Effect in the Liver and of the Hepatocyte Injury Induced by α-Galactosylceramide in Mice," *J. Immun.*, vol. 166, No. 11, pp. 6578-6584 (2001).
Pal, E. et al., "Costimulation-Dependent Modulation of Experimental Autoimmune Encephalomyelitis by Ligand Stimulation of Vα14 NK T Cells," *J. Immunol.*, vol. 166, pp. 662-668 (2001).
Park, S. et al., "CD1-restricted T-cell responses and microbial infection," *Nature*, vol. 406, pp. 788-792 (2000).
Park, S. et al. The Mouse CD1d-restricted Repetoire is Dominated by a Few Autoreactive T cell Receptor Families, *J. Exp. Med.*, vol. 8, pp. 893-904 (2001).
Petrovsky, N. et al., "Vaccine adjuvants: current state and future trends," *Immunol. Cell. Biol.*, vol. 82, pp. 488-496 (2004).
*Remington: The Science and Practice of Pharmacy*, 20th Edition, editor Daniel Limmer, published by the University of the Sciences in Philadelphia, pp. 786, 858-863 and 218-219 (2000).
Rock, K. et al., "Natural endogenous adjuvants," *Springer Semin. Immunopathol.*, vol. 26, pp. 231-246 (2005).
Sakai, T. et al., "Effects of α- and β-Galactosylated C2-Ceramides on the Immune System," *J. Med. Chem.*, vol. 41, pp. 650-652 (1998).
Sidobre, S. et al., "CD1d tetramers: a powerful tool for the analysis of glycolipid reactive T cells," *J. Immunol. Methods*, vol. 268, pp. 107-121 (2002).
Singh, A. et al., "The natural killer T cell ligand alpha-galactosylceramide protects mice against EAE by an IL-4- and IL-10-dependent mechanism," *FASEB J. Fed. of Amer. Soc. for Exp. Bio.*, vol. 16, p. A1043 (2002).
Singh, P. et al., "The Synthesis of 2,3,4,6,7-Penta-*O*-Methyl-D-*glycero*-L-*manno*-Heptose and 2,4,6,7-Tetra-*O*-Methyl-D-*glycero*-L-*manno*-Heptose," *Carbohydrate Res.*, vol. 12, pp. 261-266 (1970).
Supplementary Search Report of the European Patent Office for Application No. 03816701.1 dated Sep. 17, 2007.
Takikawa et al., "Diastereoselective Epoxidation of the Double Bond at C-4 of Sphinogosines to Provide Phytosphinogosine Relatives such as α-Galactosylceramide KRN7000," *Tetrahedron*, vol. 54, pp. 3141-3150 (1998).
U.S. Office Action for U.S. Appl. No. 10/550,165 dated Jan. 9, 2008.
U.S. Office Action for U.S. Appl. No. 10/550,165 dated Jul. 20, 2007.
Van Kaer, L. et al., "Alpha-galactosylceramide therapy for autoimmune diseases: prospects and obstacles," *Nat. Rev. Immunol.*, vol. 5, pp. 31-42 (2005).
Vaultier, M. et al., *Tetrahedron Letters*, vol. 24, p. 763 (1983).
Wang, B. et al., "CD1-Restricted NK T Cells Protect Nonobese Diabetic Mice from Developing Diabetes," *J. Exp. Med.*, vol. 194, pp. 313-319 (2001).
Wang, F. et al., "Tuning of Binding Selectivity: Metal Control of Organic Guest Binding and Allosteric Perturbation of Fluorescent Metal Sensor," *J. Org. Chem.*, vol. 64, pp. 8922-8928 (1999).
Weber, G. et al., "Synthesis and Spectral Properties of a Hydrophobic Fluorscent Probe: 6-Propionyl-2-(dimethylamino) naphthalene," *Biochem.*, vol. 18, No. 14, pp. 3075-3078 (1979).
Written Opinion of International Preliminary Examining Authority for International Application No. PCT/US03/08530 dated Jun. 30, 2005.
Wu et al., "Bacterial glycolipids and analogs as antigen for CD1d-restricted NKT cells," *PNAS*, vol. 102, No. 5, pp. 1351-1356 (2005).
Yu, K. et al., "Modulation of CD1d-restricted NKT cell responses by using N-acyl variants of alpha-galactosylceramides," *Proc. Natl. Acad. Sci. USA*, vol. 102, No. 9, pp. 3383-3388 (2005).
Zajonc, D. et al., "Structural basis for CD1d presentation of a sulfatide derived from myelin and its implications for autoimmunity," *J. Exp. Med.*, vol. 202, No. 11, pp. 1517-1526 (2005).
Zajonc, D. et al., "Structure and function of a potent agonist for the semi-invariant natural killer T cell receptor," *Nat. Immunol.*, vol. 6, pp. 810-818 (2005).
Zhou et al., "Synthesis and NKT cell stimulating properties of fluorophore-and biotin-appended 6"-amino-6"deoxy-galactosylceramides," *Org.Lett.*, vol. 4, No. 8, pp. 1267-1270 (2002).
Zhou, D. et al., "Lysosomal glycosphingolipid recognition by NKT cells," *Science*, vol. 306, pp. 1786-1789 (2004).
English et al., Secondary ion yield improvements for phosphate and sulfated molecules using substrate-enhanced time-of-flight secondary ion mass spectrometry, *International Journal of Mass Spectrometry*, vol. 2009, No. 2-3, 2001, pp. 113-124.

* cited by examiner

CD11c+, CD8a−

ADJUVANTS AND METHODS OF USE

CROSS-REFERENCE TO RELATED APPLICATIONS

This application is a divisional application of U.S. application Ser. No. 11/771,128 filed Jun. 29, 2007, which claims the benefit of U.S. Provisional Application No. 60/806,330 filed Jun. 30, 2006, the disclosures of which are incorporated by reference herein in their entirety.

STATEMENT REGARDING FEDERALLY SPONSORED RESEARCH

This invention was made with United States government support awarded by the National Institutes of Health, under grant number PO1 AI053725. The United States has certain rights in this invention.

BACKGROUND OF THE INVENTION

1. Field of the Invention

The invention relates generally to the field of immunobiology. In particular, the invention relates to compositions and methods useful in stimulating an NKT cell or enhancing an immune response against a disease or disorder.

2. Introduction

Lipid species are ubiquitous constituents of all eukaryotic membranes and pathogenic microorganisms. Despite the abundance of lipids in biological systems, the anti-lipid immune response has not been studied to the same extent as the anti-peptide response. For example, comparatively little is known about the phenomenon of non-toll-like receptor (non-TLR) recognition of lipid antigens. Unlike peptide antigens, lipids are processed and presented to the immune system by the CD1 family of β2 microglobulin-associated molecules. In contrast to class I and II major histocompatibility complex (MHC) molecules that present peptide antigens to CD8+ and CD4+ T cells, respectively, CD1 molecules have evolved to capture and process both foreign and self lipid antigens for display to particular subsets of T cells.

A variety of lipids with different structures have been shown to bind CD1 molecules in a unique manner that accommodates a fatty acid chain in each of the two hydrophobic binding pockets (A' and F) of the CD1 molecule. Lipid species capable of binding CD1 molecules include mycolic acids, diacylglycerols, sphingolipids, polyisoprenoids, lipopeptides, phosphomycoketides and small hydrophobic compounds.

The CD1 presentation pathway triggers both innate and adaptive immune responses by activating two complementary CD1-restricted T cell subsets: NKT cells that perform adjuvant functions, and non-NKT T cells capable of helper or cytolytic functions.

NKT cells, which express both natural killer (NK) cell surface markers and a conserved, semi-invariant T-cell receptor (TCR), Vα14-Jα18/Vβ8 in mice and Vα24-Jα18/Vβ11 in humans, are characterized by self lipid reactivity and rapid effector responses. Accordingly, NKT cells play an important role in a number of immune functions, including antimicrobial responses, antitumor immunity and regulation of the balance between tolerance and autoimmunity.

The apparent pluripotency of NKT cells depends specifically on their ability to interact with dendritic cells (DCs), to determine the $T_{H1}$ or $T_{H2}$ polarity of the T cell response, and to initiate T cell energy in appropriate circumstances. The maturation and recruitment process of DCs is central to their function. Indeed, DCs can rapidly progress from quiescence and low metabolic activity to active uptake of antigen, processing and tissue migration after receiving differentiation signals.

A number of natural and synthetic lipid molecules are processed by DCs and presented by CD1 molecules to NKT cells. The prototypical compound used to study NKT cell activation in vitro and in vivo is KRN7000, an α-galactosylceramide ("αGalCer") derived from marine sponge *Agelas mauritianus*. Additional agonists include isoglobotrihexosylceramide ("iGb3" or "PBS-47"), which is an endogenous glycosphingolipid, as well as members of a class of microbial-derived α-glycuronosylceramides. However, very little has been elucidated regarding anti-lipid responses in general. In the context of vaccination in particular, even less is known regarding the mechanism of lipid adjuvanticity.

Adjuvants are used to augment the immune response in anti-microbial and anti-tumor vaccination protocols, as well as in experimental immunology. The chemical nature of adjuvants, their mechanisms of action and their side effect profiles are highly variable. In some cases, side effects can be ascribed to an inappropriate immune response, or in other cases, can be the result of adverse pharmacological reactions. At present, the choice of adjuvant for human vaccination reflects a compromise between the requirement for adjuvanticity and an acceptable level of side effects.

SUMMARY OF THE INVENTION

In one aspect, the invention provides a composition comprising a compound represented by structural formula (I):

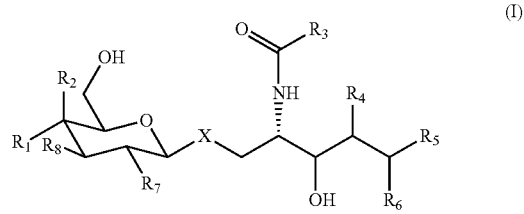

wherein: X is —O—, —CH$_2$— or —S—; R$_1$ is —H, —OH, —OSO$_3$H, —SO$_3$H, —PO$_4$, —PO$_4$H, —COOH or a group represented by structural formula (II):

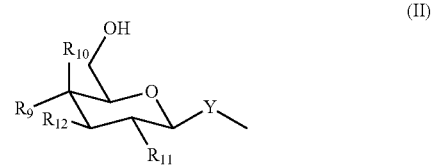

wherein: Y is —O—, —CH$_2$— or —S—; R$_9$, R$_{10}$, R$_{11}$ and R$_{12}$ are independently selected from —H, —OH, —OSO$_3$H, —SO$_3$H, —PO$_4$, —PO$_3$H and —COOH; R$_2$ is selected from —H, OSO$_3$H, —SO$_3$H and —PO$_4$; R$_7$ and R$_9$ are independently selected from —H, —OH—OSO$_3$H—SO$_3$H, —PO$_4$, —PO$_4$H and —COOH; R$_3$ is a saturated or unsaturated hydrocarbon group having about 7 to about 25 carbon atoms; R$_4$ is —H, —OH, or, together with R$_6$, forms a carbon-carbon double bond; R$_5$ is a saturated or unsaturated hydrocarbon group having from about 5 to about 15 carbon atoms, and R$_6$ is —H, —OH, or together with R$_4$ forms a C—C double bond, provided that at least one of $R_1$, $R_2$, $R_7$, $R_8$, $R_9$, $R_{10}$, $R_{11}$ or $R_{12}$ is —H, —OH, —OSO$_3$H, —SO$_3$H, —PO$_4$, —PO$_4$H or —COOH; and a physiologically acceptable vehicle.

In another aspect, the invention provides a composition comprising a compound represented by structural formula (I):

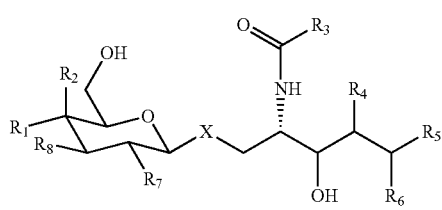

wherein: X is —O—, —CH$_2$— or —S—; $R_1$ is —H, —OH, —OSO$_3$H, —SO$_3$H, —PO$_4$, —PO$_4$H, —COOH or a group represented by structural formula (II):

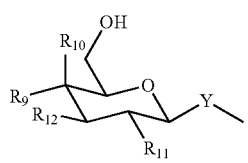

wherein: Y is —O—, —CH$_2$— or —S—; $R_9$, $R_{10}$, $R_{11}$ and $R_{12}$ are independently selected from —H, —OH, —OSO$_3$H, —SO$_3$H, —PO$_4$, —PO$_3$H and —COOH; $R_2$ is selected from —H, —OH, OSO$_3$H, —SO$_3$H and —PO$_4$; $R_3$ is a saturated or unsaturated hydrocarbon group having from about 7 to about 25 carbon atoms; $R_4$ is —H, —OH, or, together with $R_6$, forms a carbon-carbon double bond; $R_5$ is a saturated or unsaturated hydrocarbon group having from about 5 to about 15 carbon atoms; $R_6$ is —H, —OH, or together with $R_4$ forms a C—C double bond; $R_7$ is selected from —H, —OH, —OSO$_3$H, SO$_3$H, —PO$_4$, —PO$_4$H and —COOH; and $R_8$ is selected from —H, —OH, —PO$_4$, —PO$_4$H and —COOH; provided that at least one of $R_1$, $R_2$, $R_7$, $R_8$, $R_9$, $R_{10}$, $R_{11}$ or $R_{12}$ is —H, —OH, —OSO$_3$H, —SO$_3$H, —PO$_4$, —PO$_4$H or —COOH; and a physiologically acceptable vehicle.

In some embodiments, the composition optionally includes an antigen. Some embodiments of the invention provide the composition formulated as a vaccine preparation.

In a further aspect, the invention provides a method of stimulating an NKT cell comprising contacting the NKT cell with a compound having a structural formula represented by formula (I). In some embodiments, the NKT cell is cultured in vitro, while in other embodiments, the NKT cell is within a subject, or "in vivo."

In another aspect, the invention provides a method of enhancing an immune response in a subject. The method includes administering the compound of formula (I) to the subject. In some embodiments, the compound of formula (I) is co-administered with an antigen.

In a still further aspect, the invention provides a vaccine preparation, formulated to include a compound of formula (I) and a physiologically acceptable vehicle.

BRIEF DESCRIPTION OF THE DRAWINGS

FIG. 9 graphically represents the ability of PBS-32 to act as an adjuvant when administered with an ovalbumin nominal antigen.

FIG. 11 is a graph showing IgM and IgG anti-GM3 antibody concentration, as measured by ELISA, after biweekly immunization with GM3 in combination with a lipid transfer protein (either CD14, LBP, ApoH, NPC-2, GM2A or saposin B) and αGalCer. Each bar represents a separate bleed (every other week).

DESCRIPTION OF ILLUSTRATIVE EMBODIMENTS

Figure 1:
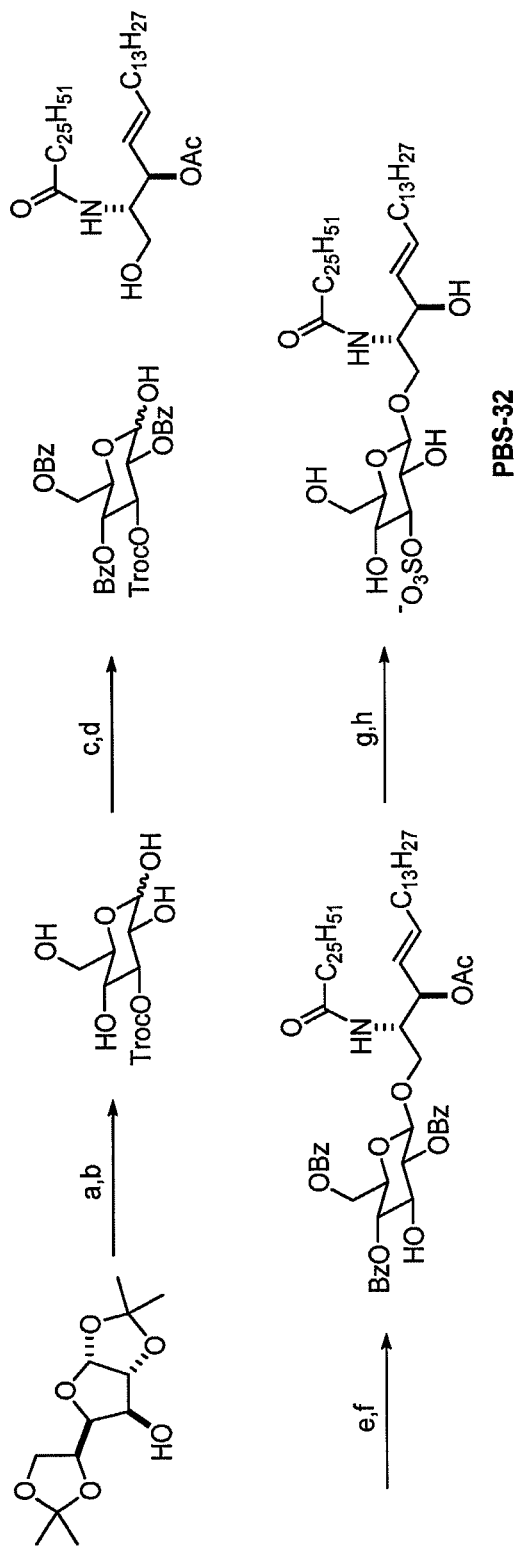
FIG. 1 depicts a suitable synthetic scheme for sulfoglucosylceramide (SuGC), also referred to herein as PBS-32.

The inventors have discovered that an endogenous sulfoglucosylceramide, designated "PBS-32," and its phytoceramide counterpart, designated "PBS-31," are strong agonists of NKT cells. As such, these compounds can enhance an immune response in a subject under appropriate circumstances. Because they are endogenous compounds, the likelihood of side effects is reduced in comparison to exogenous adjuvants. Similarly, variants of these compounds that have been modified, e.g., to introduce properties suitable for in vivo delivery, are also expected to exhibit a reduced likelihood of side effects. As further described below, suitable variants include modifications of the sulfate group, the ceramide head group, the sugar linkage, the fatty acid and the sphingosine side chain of PBS-32. PBS-32 and variants of this compound that exhibit NKT cell agonist activity are collectively referred to herein as "NKT cell agonist compounds."

NKT cell agonist compounds have a structure represented by formula (I):

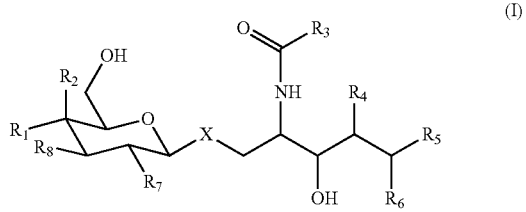

(I)

wherein:
X is —O—, —CH$_2$— or —S—;
R$_1$ is —H, —OH, —OSO$_3$H, —SO$_3$H, —PO$_4$, —PO$_4$H, —COOH or a group represented by structural formula (II):

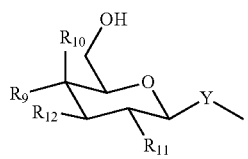

(II)

wherein:
Y is —O—, —CH$_2$— or —S—;
R$_3$, R$_{10}$, R$_{11}$ and R$_{12}$ are independently selected from —H, —OH, —OSO$_3$H,
—SO$_3$H, —PO$_4$, —PO$_3$H and —COOH;
R$_2$, R$_7$ and R$_8$ are independently selected from —H, —OH—OSO$_3$H—SO$_3$H, —PO$_4$,
—PO$_4$H, and —COOH;
R$_3$ is a saturated or unsaturated hydrocarbon group having about 7 to about 25 carbon atoms;
R$_4$ is —H, —OH, or, together with R$_6$, forms a carbon-carbon double bond; and
R$_5$ is a saturated or unsaturated hydrocarbon group having about 5 to about 15 carbon atoms, provided that at least one of R$_1$, R$_2$, R$_7$, R$_8$, R$_9$, R$_{10}$, R$_{11}$ or R$_{12}$ is —H, —OH, —OSO$_3$H,
—SO$_3$H, —PO$_4$, —PO$_4$H, or —COOH.

As used herein, the term "saturated or unsaturated hydrocarbon" refers to straight-chain alkyl or alkenyl groups of specified lengths. Alkenyl groups include one or more double bonds. Suitably, alkenyl groups of compounds of formula (I) may include from about 1 to about 3 carbon-carbon double bonds.

Suitable NKT cell agonist compounds may include, but are not limited to, PBS-32 and PBS-31. Non-limiting examples of further suitable NKT cell agonist compounds having a modified glycoside bond and/or sulfate group are shown below:

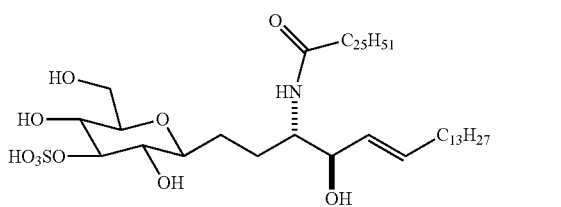

BSG-1

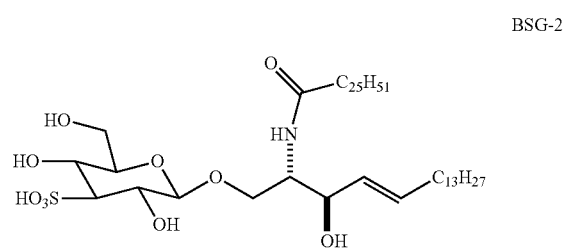

BSG-2

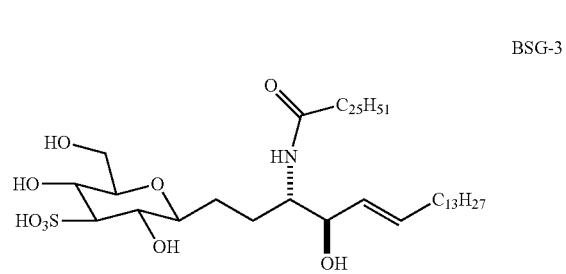

BSG-3

Non-limiting examples of suitable NKT cell agonist compounds having modified lipid chains are shown below:

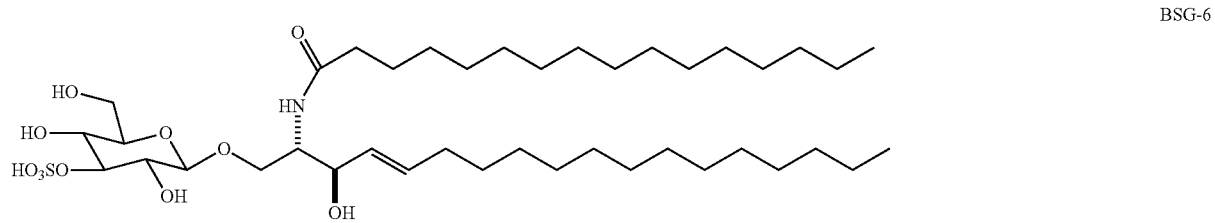

BSG-6

-continued
BSG-7
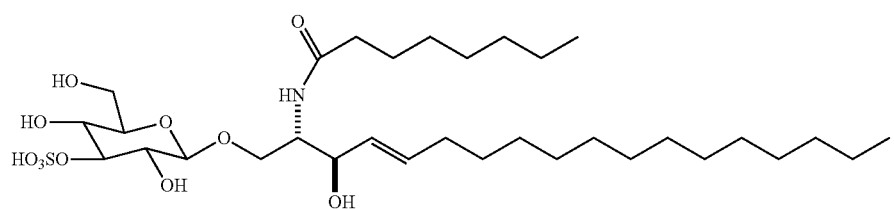
BSG-8
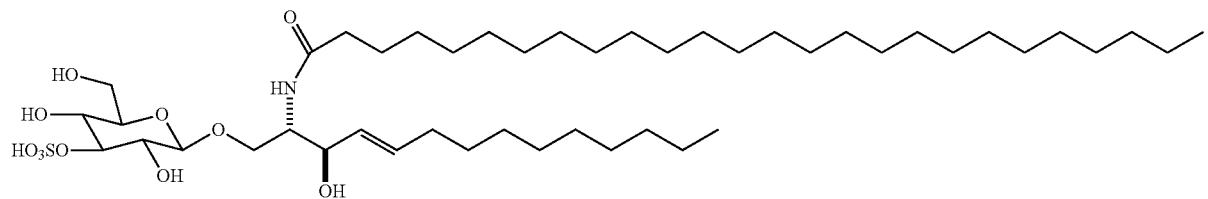
BSG-9
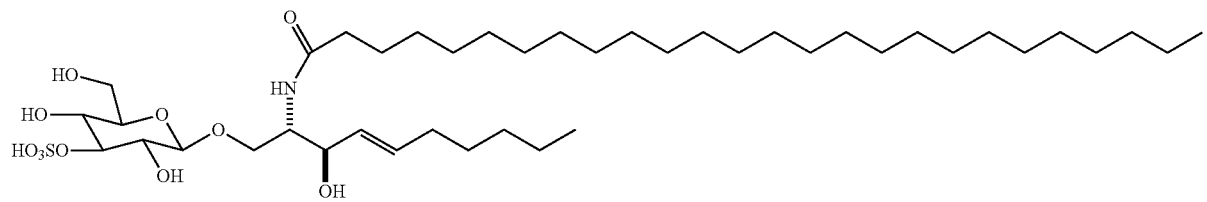
BSG-10
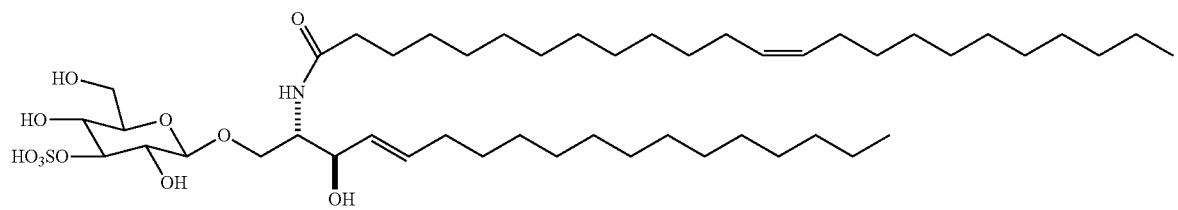
BSG-11
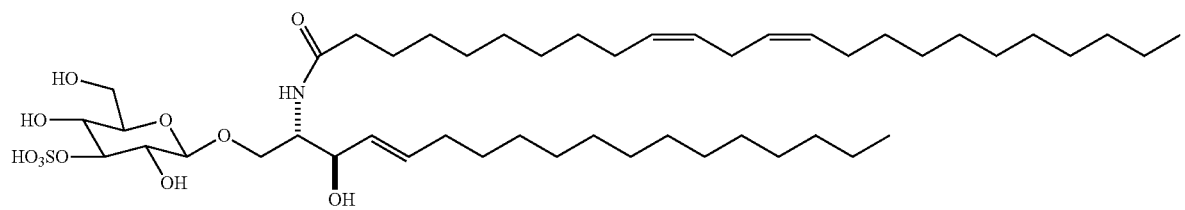
Non-limiting examples of suitable NKT cell agonist compounds having modified ceramide chains are shown below:
-continued
BSG-12
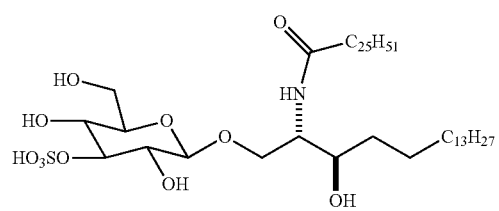
PBS-31
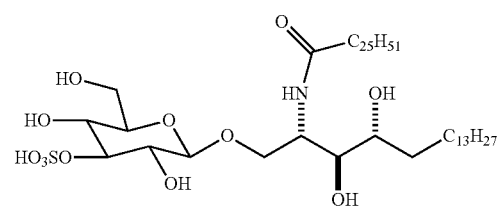

-continued

BSG-13
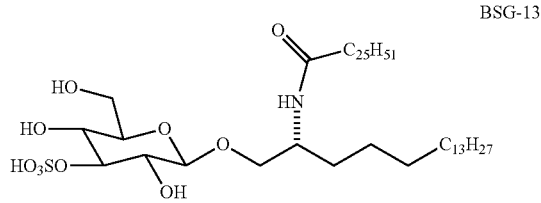

Non-limiting examples of suitable NKT cell agonist compounds having modified carbohydrate groups are shown below:

BSG-14
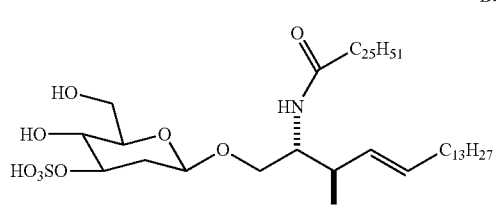

BSG-15
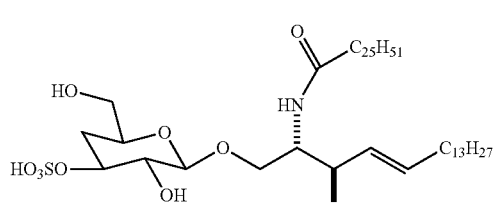

BSG-16
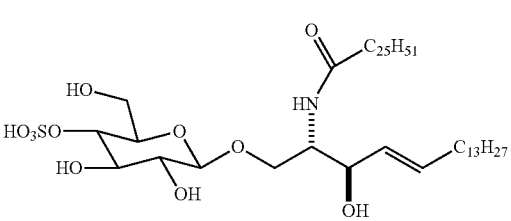

BSG-17
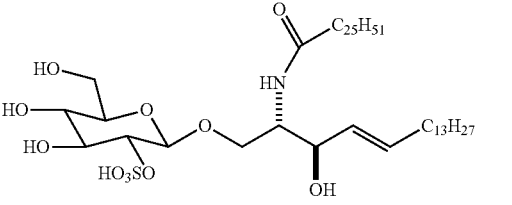

BSG-18
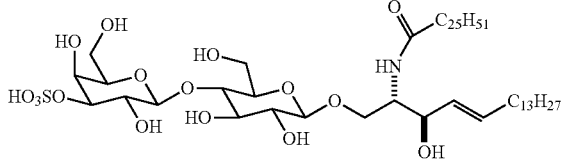

Endogenous NKT cell agonist compounds may be purified from natural sources using any suitable method known in the art. Alternatively, the NKT cell agonist compounds may be chemically synthesized. One suitable scheme for synthesis of NKT cell agonist compounds is described in Example 1, below. Variant compounds may be synthesized by modifications of the method, as may be derived from Zhou, D et al., *Science* 306: 1786-1789 (2004); Goff, R. D. et al., *J. Am. Chem. Soc.* 126: 13602-13603 (2004); and Marshall, R. L. et al. *Tetrahedron Lett.*, 39: 3923-3926 (1998), each of which are incorporated herein by reference in their entireties.

Compositions

NKT cell agonist compounds, as described above, are suitably included in a composition with a physiologically acceptable vehicle. A "physiologically acceptable" vehicle is any vehicle that is suitable for in vivo administration (e.g., oral, transdermal or parenteral administration) or in vitro use, i.e., cell culture. Suitable physiologically acceptable vehicles for in vivo administration include water, buffered solutions and glucose solutions, among others. A suitable vehicle for cell culture is commercially available cell media. Additional components of the compositions may suitably include excipients such as stabilizers, preservatives, diluents, emulsifiers or lubricants, in addition to the physiologically acceptable vehicle and the NKT cell agonist compound. In particular, suitable excipients include, but are not limited to, Tween 20, DMSO, sucrose, L-histadine, polysorbate 20 and serum.

Suitably, compositions comprising NKT cell agonist compounds may be formulated for in vivo use, i.e., therapeutic or prophylactic administration to a subject. In some embodiments, the compositions are formulated for parenteral administration. A suitable dosage form for parenteral administration is an injectable. An injectable dosage form may be an isotonic solution or suspension and may be prepared using a suitable dispersion agent, wetting agent or suspension agent, as known in the art. In other embodiments, the compositions are formulated for oral administration. Suitable oral dosage forms include tablets, capsules, syrups, troches and wafers, among others. Oral dosage formulations suitably include lactose, starch, cellulose derivatives, magnesium stearate, stearic acid, glycols, and others. It will be appreciated that the compositions of the invention are not limited to any particular exemplified dosage form, but can be formulated in any manner described in the art, for example, in Remington's Pharmaceutical Sciences, Mack Publishing Co., (2000), which is incorporated herein by reference.

In addition to the NKT cell agonist compound and a physiologically acceptable vehicle, some embodiments of the invention further include an antigen and are suitably formulated as a vaccine preparation. Antigens included in the vaccine preparation may be polypeptide or carbohydrate moieties, or combinations thereof, for example, glycoproteins. The antigen may be derived from an infectious agent (e.g., a pathogenic microorganism), a tumor, an endogenous molecule (e.g., a "self" molecule), or, for purposes of study, a nominal antigen, such as ovalbumin. The vaccine may be formulated using a variety of preparative methods known to those of skill in the art. See Remington's Pharmaceutical Sciences, Mack Publishing Co., (2000), which is incorporated herein by reference.

In some embodiments, antigens for inclusion in compositions of the invention are suitably derived from attenuated or killed infectious agents. It will be understood that whole microorganisms or portions thereof (e.g., membrane ghosts; crude membrane preparations, lysates and other preparations of microorganisms) may suitably be included as an antigen. Suitable infectious agents from which an antigen may be derived include, but are not limited to, pathogenic viruses and microorganisms. In some contexts, suitable antigens are obtained or derived from a viral pathogen that is associated with human disease including, but not limited to, HIV/AIDS (Retroviridae, e.g., gp120 molecules for HIV-1 and HIV-2 isolates, HTLV-I, HTLV-11), influenza viruses (Orthomyxoviridae, e.g., types A, B and C), herpes (e.g., herpes simplex viruses, HSV-1 and HSV-2 glycoproteins gB, gD and gH), rotavirus infections (Reoviridae), respiratory infections (parainfluenza and respiratory syncytial viruses), Poliomyelitis (Picornaviridae, e.g., polioviruses, rhinoviruses), measles and mumps (Paramyxoviridae), Rubella (Togaviridae, e.g., rubella virus), hepatitis (e.g., hepatitis viruses types A, B, C, D, E and/or G), cytomegalovirus (e.g., gB and gH), gastroenteritis (Caliciviridae), Yellow and West Nile fever (Flaviviridae), Rabies (Rhabdoviridae), Korean hemorrhagic fever (Bunyaviridae), Venezuelan fever (Arenaviridae), warts (Papillomavirus), simian immunodeficiency virus, encephalitis virus, varicella zoster virus, Epstein-Barr virus, and other virus families, including Coronaviridae, Birnaviridae and Filoviridae.

Suitable bacterial and parasitic antigens can also be obtained or derived from known bacterial agents responsible for diseases including, but not limited to, diphtheria, pertussis, tetanus, tuberculosis, bacterial or fungal pneumonia, otitis media, gonorrhea, cholera, typhoid, meningitis, mononucleosis, plague, shigellosis or salmonellosis, Legionnaires' disease, Lyme disease, leprosy, malaria, hookworm, Onchocerciasis, Schistosomiasis, Trypanosomiasis, Leishmaniasis, giardiases, amoebiasis, filariasis, *Borrelia*, and trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Specific pathogens from which antigens can be derived include *M. tuberculosis, Chlamydia, N. gonorrhoeae, Shigella, Salmonella, Vibrio cholerae, Treponema pallidum, Pseudomonas, Bordetella pertussis, Brucella, Francisella tularensis, Helicobacter pylori, Leptospira interrogans, Legionella pneumophila, Yersinia pestis, Streptococcus* (types A and B), *pneumococcus, meningococcus, Haemophilus influenza* (type b), *Toxoplasma gondii, Moraxella catarrhalis*, donovanosis, and actinomycosis; fungal pathogens include candidiasis and aspergillosis; parasitic pathogens include *Taenia*, flukes, roundworms, amebiasis, giardiasis, *Cryptosporidium, Schistosoma, Pneumocystis carinii*, trichomoniasis and trichinosis. The present invention can also be used to provide a suitable immune response against numerous veterinary diseases, such as foot-and-mouth diseases, coronavirus, *Pasteurella multocida, Helicobacter, Strongylus vulgaris, Actinobacillus pleuropneumoniae*, Bovine Viral Diarrhea Virus (BVDV), *Klebsiella pneumoniae, E. coli*, and *Bordetella pertussis, parapertussis* and *brochiseptica*.

In some embodiments, antigens for inclusion in compositions of the invention are suitably tumor-derived antigens or autologous or allogeneic whole tumor cells. Suitably, the tumor antigen is a tumor specific antigen (TSA) or a tumor associated antigen (TAA). Several tumor antigens and their expression patterns are known in the art and can be selected based on the tumor type to be treated. Non-limiting examples of tumor antigens include cdk4 (melanoma), β-catenin (melanoma), caspase-8 (squamous cell carcinoma), MAGE-1 and MAGE-3 (melanoma, breast, glioma), tyrosinase (melanoma), surface Ig idiotype (e.g., BCR) (lymphoma), Her-2/neu (breast, ovarian), MUC-1 (breast, pancreatic) and HPV E6 and E7 (cervical carcinoma). Additional suitable tumor antigens include prostate specific antigen (PSA), sialyl Tn (STn), heat shock proteins and associated tumor peptides (e.g., gp96), ganglioside molecules (e.g., GM2, GD2, and GD3), Carcinoembryonic antigen (CEA) and MART-1.

Methods of Stimulating NKT Cells

"Stimulating an NKT cell" and "activating an NKT cell" are used interchangeably herein to refer to inducing an observable effect in an NKT cell that is consistent with a cellular response to engagement of the TCR of the NKT cell with an antigen presented in the context of CD1d. Observable effects of stimulation of NKT cells include secretion of cytokines, clonal proliferation and upregulation of expression of cell surface markers, for example, CD69 molecules, IL-12 receptors and/or CD40L molecules. To stimulate an NKT cell in accordance with the present methods, the NKT cell is contacted with a NKT cell agonist compound in an amount sufficient to induce any of the above-listed observable effects.

As used herein, "contacting an NKT cell" refers to the in vitro addition of an NKT cell agonist compound to NKT cells in culture, optionally in the presence of immobilized, soluble, or insoluble CD1d molecules or APCs expressing CD1d molecules, or to the in vivo administration of NKT cell agonist compound to a subject.

The NKT cell agonist compound may be presented to the TCR of the NKT cell by CD1d molecules on the surface of an antigen presenting cell (APC), such as a dendritic cell (DC). Alternatively, CD1d molecules may be plated and the NKT cells and NKT cell agonist compound can be added to the CD1d molecules in vitro. In some in vitro embodiments, a lipid transfer molecule, e.g., saposin B, may be used to facilitate loading of CD1d molecules with NKT cell agonist compounds.

Examples of cytokines that may be secreted by NKT cells stimulated in accordance with the invention may include, but are not limited to, IL-10, IL-4, and IL-12, IL-13, GM-CSF, IFN-γ, IL-2, IL-1, IL-6, IL-8, TNF-α, and TGF-β. It is appreciated that combinations of any of the above-noted cytokines may be secreted by NKT cells upon activation. Methods for detecting and measuring levels of secreted cytokines are well-known in the art.

NKT cell proliferation may also be induced upon stimulation by contact with NKT cell agonist compounds. Proliferation is suitably measured in vitro by standard methods, e.g. $^3$H-thymidine or BrdU incorporation assays.

Upregulation of cell surface markers is also suitably observed upon activation of NKT cells. For example, CD69, CD25, CD40L and IL-12 receptors are upregulated upon activation of NKT cells. Immunologic methods, such as FACS, may be used to detect upregulation of cell surface markers, as well as other methods commonly employed in the art. Downstream effects of NKT cell activation, such as induction of DC maturation, are also observable, e.g., by measuring upregulation of CD80 and/or CD86 on DCs.

In vivo and ex vivo activation of NKT cells is specifically contemplated in addition to in vitro activation. Presentation of NKT cell agonist compounds to NKT cells results in NKT cell activation and dendritic cell maturation. Consequently, these compounds stimulate immune responses against nominal antigens as well as infectious agents and neoplastic malignancies, including solid and hematologic tumors. Both cellular and humoral immunity may be stimulated by administering NKT cell agonist compounds.

Methods of stimulating an NKT cell in vivo, i.e., in a subject, include administering a NKT cell agonist compound to the subject. Administration to a subject in accordance with some methods of the invention may include first formulating the NKT cell agonist compound with a physiologically acceptable vehicle and/or excipient to provide desired dosages, stability, etc. Suitable formulations for vaccine preparations and therapeutic compounds are known in the art.

Methods of stimulating an NKT cell ex vivo may include use of adoptive transfer methods based on administering cells that have been contacted with NKT cell agonist compounds ex vivo to stimulate NKT cells in a subject. In some embodiments, the cells may be NKT cells that are stimulated ex vivo and injected into a subject. In other embodiments, the cells may be APCs that have been contacted with NKT cell agonist compounds ex vivo to allow loading of the CD1d molecules with the NKT cell agonist compound for presentation to NKT cells. The ex vivo stimulated NKT cells or loaded APCs can then be administered, e.g., by injection into the subject.

Methods of Enhancing an Immune Response

Some embodiments of the invention provide a method of enhancing an immune response in a subject. A "subject" is a vertebrate, suitably a mammal, more suitably a human. As will be appreciated, for purposes of study, the subject is suitably an animal model, e.g., a mouse. "Enhancing an immune response" includes, but is not limited to, inducing a therapeutic or prophylactic effect that is mediated by the immune system of the subject. More specifically, enhancing an immune response in the context of the invention refers to eliciting an NKT cell response in a subject by administering an NKT cell agonist compound, thereby inducing downstream effects such as production of antibodies, antibody heavy chain class switching, maturation of APCs, and stimulation of cytolytic T cells, T helper cells and both T and B memory cells.

In some embodiments, the immune response enhanced according to the invention may be an antimicrobial immune response. Such an immune response suitably promotes clearance of an infectious agent or permits immune control of the agent such that disease symptoms are reduced or resolved, e.g., a persistent or latent infection.

In other embodiments, the enhanced immune response may be an anticancer or antitumor immune response. Such an immune response suitably promotes tumor rejection, reduces tumor volume, reduces tumor burden, prevents metastasis, and/or prevents recurrence of the tumor. The tumor may be any solid or hematologic tumor, including but not limited to leukemia, lymphoma, AIDS-related cancers, cancers of the bone, brain, breast, gastrointestinal system, endocrine system, eye, genitourinary tract, germ cells, reproductive organs, head and neck, musculoskeletal system, skin, nervous system or respiratory system. As is appreciated in the art, a cancer-specific immune response may be monitored by several methods, including: 1) measuring cytotoxicity of effector cells, using, e.g., a chromium release assay; 2) measuring cytokine secretion by effector cells; 3) evaluating T cell receptor (TCR) specificities, e.g., by using MHC-peptide multimers; 4) measuring the clonal composition of the T cell response; and/or 5) measuring T cell degranulation.

An enhanced immune response is also suitably assessed by the assays described in the examples below. In particular, the examples demonstrate that in some embodiments, NKT cell agonist compounds are capable of activating NKT cells, inducing cytokine production, inducing maturation of APCs, enhancing cytolytic and helper T cell functions, enhancing CD8+ and CD4+ T cell recruitment, enhancing antibody production, inducing antibody class switching and breaking tolerance.

Enhancing an immune response in a subject in accordance with the invention may be accomplished by administering to the subject a composition including an NKT cell agonist compound and in some embodiments, an antigen. The NKT cell agonist compound and the antigen may or may not induce a detectably enhanced immune response when administered to a subject independently. However, in accordance with the invention, co-administration of an NKT cell agonist compound and an antigen leads to an enhanced immune response in vaccinated or treated subjects as compared to unvaccinated or untreated subjects.

Suitably, the NKT cell agonist compound and the antigen are co-administered. The term "co-administration" is meant to refer to any administration protocol in which a NKT cell agonist compound and an antigen are administered to a subject. The NKT cell agonist compound and the antigen may be in the same dosage formulations or separate formulations. Where the NKT cell agonist compound and antigen are in separate dosage formulations, they can be administered concurrently, simultaneously or sequentially (i.e., administration of one may directly follow administration of the other or they may be given episodically, i.e., one can be given at one time followed by the other at a later time, e.g., within a week), as long as they are given in a manner sufficient to allow both to achieve therapeutically or prophylactically effective amounts in the subject. The NKT cell agonist compound and the antigen may also be administered by different routes, e.g., one may be administered intravenously while the second is administered intramuscularly, intravenously or orally.

In some embodiments, the NKT cell agonist compound is suitably added to a vaccine composition or is co-administered with a vaccine composition. Addition of an NKT cell agonist compound to a vaccine composition or co-administration with a vaccine composition may be particularly suitable in cases where the antigen has a low rate of efficacy as a vaccine and/or must be administered in an amount or at a dose greater than what might be considered ideal due to side effects, cost and/or availability of the antigen, etc. Examples of such vaccines may include, but are not limited to human papillomavirus vaccines, acute otitis media vaccine (PREVNAR®), influenza vaccines, cholera vaccines and the telomerase cancer vaccine.

Administration to a subject may be carried out by any suitable method, including intraperitoneal, intravenous, intramuscular, subcutaneous, transcutaneous, oral, nasopharyngeal or transmucosal absorption, among others. Suitably, the NKT cell agonist compound is administered in an amount effective to activate an NKT cell or cells such that a prophylactic or therapeutic effect is achieved in the subject, e.g., an antitumor immune response or antimicrobial immune response.

Administration to a subject also includes use of adoptive transfer methods based on administering cells that have been contacted with NKT cell agonist compounds ex vivo to stimulate or enhance an immune response in a subject. In some embodiments, the cells may be NKT cells that are activated ex vivo and injected into a subject to provide or enhance an immune response to, e.g., cancerous cells or infectious agents. In some embodiments, the cells may be APCs that have been contacted with NKT cell agonist compounds ex vivo to allow complexing with the CD1d molecules expressed by the APC. Antigen presenting cells can then be administered, e.g., by injection into the subject, to provide a suitable immune response. This method of administration allows for stimulation of the immune response with minimal exposure of the subject or the subject's cells to the NKT cell agonist compounds.

Administration of NKT cell agonist compounds to a subject in accordance with the invention appears to exhibit beneficial effects in a dose-dependent manner. Thus, within broad limits, administration of larger quantities of NKT cell agonist compounds is expected to activate greater numbers of NKT cells or activate NKT cells to a greater degree than does administration of a smaller amount. Moreover, efficacy is also contemplated at dosages below the level at which toxicity is seen. Further, in practice, higher doses are generally used where the therapeutic treatment of a disease state is the desired end, while the lower doses are generally used for prophylactic purposes.

It will be appreciated that the specific dosage administered in any given case will be adjusted in accordance with the specific NKT cell agonist compound or compounds being administered, the disease to be treated or prevented, the condition of the subject, and other relevant medical factors that may modify the activity of the NKT cell agonist compound or the response of the subject, as is well known by those skilled in the art. For example, the specific dose for a particular patient depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the NKT cell agonist compound and of a known agent such as αGalCer, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. It is anticipated that dosages of NKT cell agonist compound in accordance with the present invention will prevent or reduce symptoms at least 50% compared to pre-treatment symptoms. It is specifically contemplated that vaccine preparations and compositions of the invention may palliate or alleviate symptoms of the disease without providing a cure, or, in some embodiments, may be used to cure or prevent the disease or disorder.

Suitable effective dosage amounts for administering NKT cell agonist compounds may be determined by those of skill in the art, but typically range from about 1 microgram to about 10,000 micrograms per kilogram of body weight weekly, although they are typically about 1,000 micrograms or less per kilogram of body weight weekly. In some embodiments, the effective dosage amount ranges from about 10 to about 5,000 micrograms per kilogram of body weight weekly. In another embodiment, the effective dosage amount ranges from about 50 to about 1,000 micrograms per kilogram of body weight weekly. In another embodiment, the effective dosage amount ranges from about 75 to about 500 micrograms per kilogram of body weight weekly. The effective dosage amounts described herein refer to total amounts administered, that is, if more than one NKT cell agonist compound is administered, the effective dosage amounts correspond to the total amount administered. The NKT cell agonist compound can be administered as a single weekly dose or as divided doses.

In some embodiments, a tumor antigen and the NKT cell agonist compound are co-administered to a subject to induce an anti-tumor immune response in the subject. Suitably, co-administration of the antigen with the NKT cell agonist compound enhances the anti-tumor response and results in inhibition of tumor growth, reduction in tumor burden and treatment of cancer, as described above.

Administration of a vaccine preparation or composition of the invention may suitably result in therapeutic or prophylactic treatment of an infectious disease or a disease related to an infectious agent. "Treating" or "treatment" of an infectious disease includes one or more of: (1) inhibiting infection, i.e. preventing the infectious agent from establishing an infection, (2) preventing spread of the infectious agent, i.e. to other areas of the subject or from one subject to another, (3) limiting disease severity, (4) preventing recurrent infections, i.e. limiting reactivation of latent or persistent infections, and (5) palliating symptoms of the infectious disease.

It is specifically contemplated that any embodiment of any method or composition of the invention may be used with any other method or composition of the invention.

As used in this specification and the appended claims, the singular forms "a," "an," and "the" include plural referents unless the content clearly dictates otherwise. Thus, for example, reference to a composition containing "a virus" includes a mixture of two or more viruses. It should also be noted that the term "or" is generally employed in its sense including "and/or" unless the content clearly dictates otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

The following examples are provided to assist in a further understanding of the invention. The particular materials and conditions employed are intended to be further illustrative of the invention and are not limiting on the reasonable scope of the appended claims.

EXAMPLES

Example 1

Synthesis of PBS-32

PBS-32 was synthesized as shown in FIG. 1. Reagents used in the synthesis were as follows (yields in parenthesis): a) TrocCl, pyridine, $CH_2Cl_2$ (77%), b) TFA, $H_2O$, c) BzCl, pyridine, DMAP (60% for two steps), d) 1) HBr, AcOH, $H_2O$, 2) $Ag_2CO_3$, acetone, $H_2O$ (51%), e) 1) $K_2CO_3$, $CCl_3CN$, 2) protected ceramide, $BF_3OEt_2$, MS $AW_{300}$, $CH_2Cl_2$ (56%), f) Zn/Cd, AcOH (67%), g) $SO_3$-pyridine, DMF (83%), h) NaOMe, THF, MeOH (87%).

Starting from diacetone glucose, a trichloroethoxycarbonate ("Troc") protecting group was added, and the acetals were hydrolyzed to give the pyranose form of the sugar. The remaining hydroxyl groups were protected as benzoates, and the anomeric hydroxyl group was liberated by a two-step process in which an anomeric bromide was incorporated by hydrolysis. Coupling of the protected carbohydrate with a protected ceramide was achieved using trichloroacetimidate chemistry. The Troc group wan then selectively removed and the sulfate at C3" was incorporated. Deprotection with methoxide yielded PBS-32 as a white solid.

Example 2

Loading of CD1d Molecules with Synthetic NKT Cell Agonist Compounds

Figure 2:
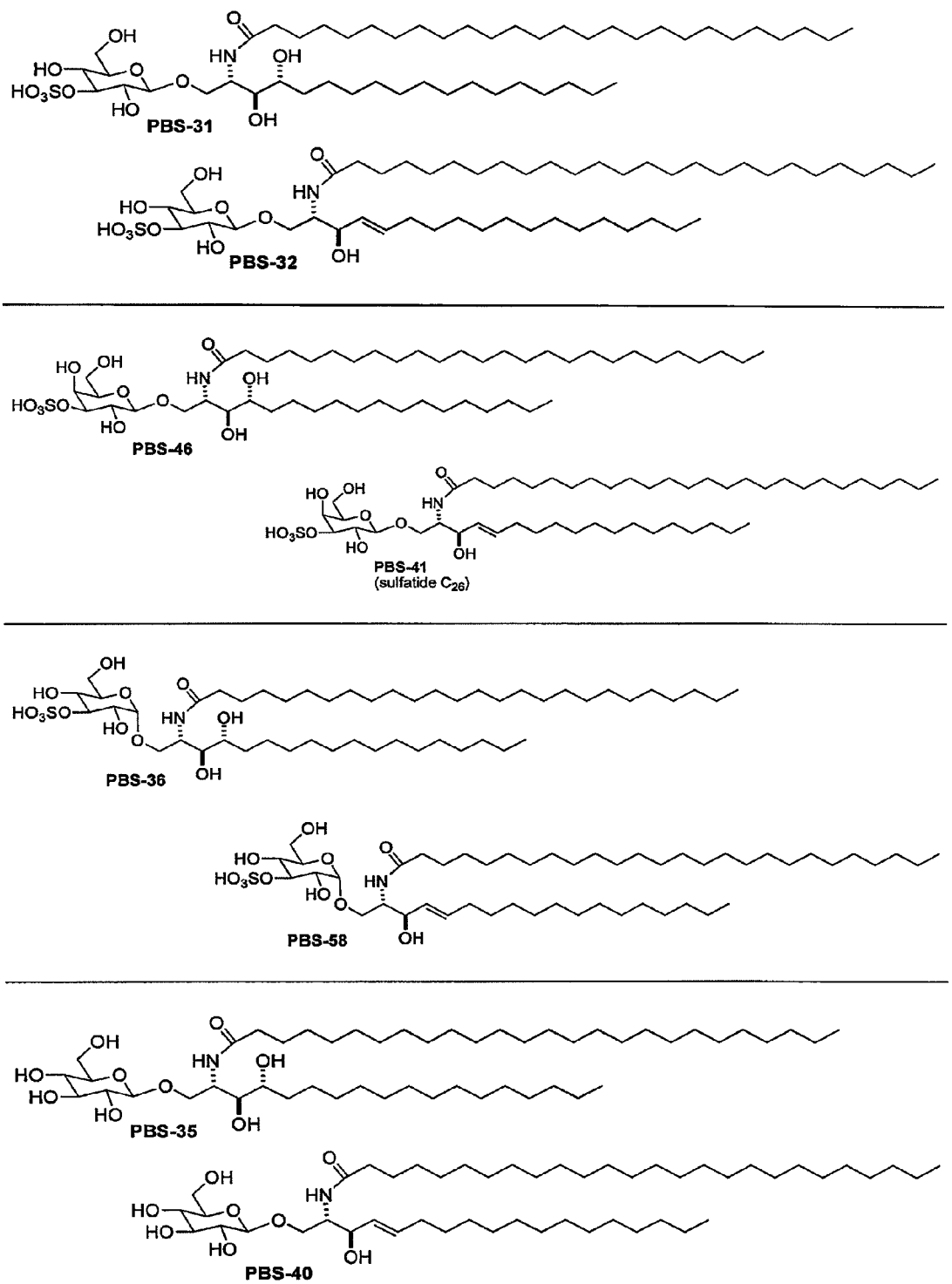
FIG. 2 depicts the structural formulae for several compounds referenced herein, including PBS-32 and modified ceramide compounds designated PBS-31 (phytoceramide) PBS-46, PBS-41 (sulfatide), PBS-36, PBS-58, PBS-35 and PBS-40.

Whether PBS-31 and PBS-32 could be efficiently loaded onto CD1d molecules was tested using a native isoelectric focusing (IEF) gel assay in the presence and absence of saposin B. For comparison, PBS-41 and PBS-46 (sulfo-β-galactosylceramides), PBS-36 and PBS-58 (sulfo-α-glucosylceramides) and PBS-35 and PBS-40 (β-glucosylceramides) were also evaluated in this assay. Structural formulae for these compounds are shown in FIG. 2.

Each 5 μl reaction contained 2 μM CD1d, 20 μM lipid and 10 μM saposin B. Reactions were incubated for 1 hour at 37° C. prior to gel loading.

Figure 3:
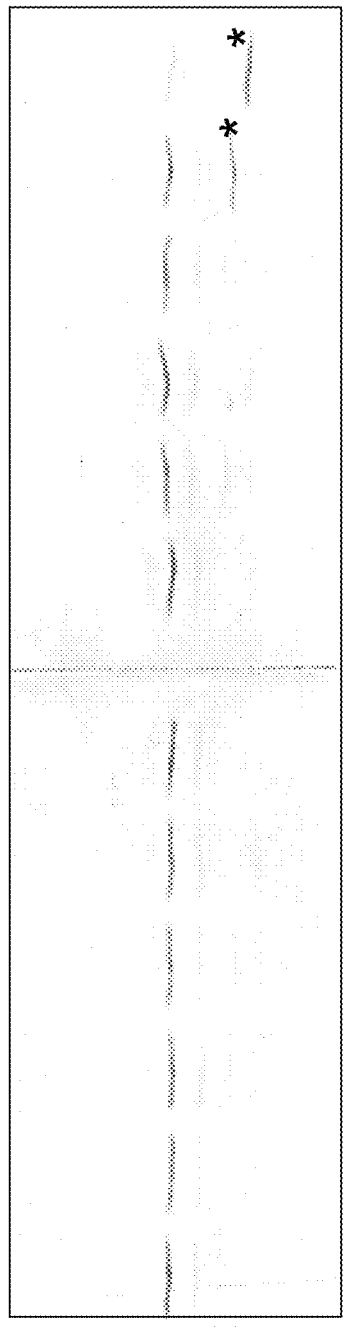
FIG. 3 is a photograph of an isoelectric focusing gel showing loading of CD1d molecules with PBS-31, PBS-32, PBS-41, PBS-46, PBS-36, PBS-58, PBS-35 and PBS-40 in the presence and absence of saposin B, a lipid transfer glycoprotein.
Figure 3:
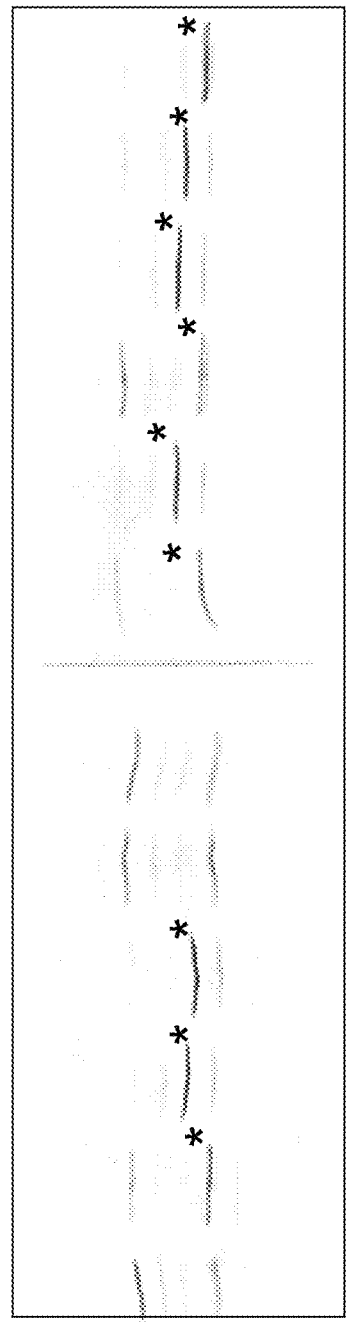

Loaded species are indicated by a star in FIG. 3. The lanes of FIG. 3 were loaded as follows: 1, no lipid; 2, αGalCer; 3, PBS-31; 4, PBS-32; 5, no lipid; 6, iGB3; 7, PBS-40; 8, PBS-41; 9, PBS-35; 10, PBS-46; 11, PBS-58; 12, PBS-25 (positive control). As indicated in FIG. 3, saposin B was required for efficient loading of CD1d molecules with all lipid species tested, with the exception of PBS-58 and PBS-25, the positive control, which were marginally loaded in the absence of saposin B. PBS-36, the phytoceramide form of PBS-58, also loaded onto CD1d in the absence of saposin B (data not shown).

Example 3

Stimulation of an NKT Cell Hybridoma by PBS-31 and PBS-32

Compounds PBS-31, PBS-32, and control lipids were evaluated for their ability to stimulate a canonical CD1d-restricted Vα14 NKT hybridoma cell, DN32.D3 in an assay described by Lantz, et al., J. Exp. Med. 180: 1097-1106 (1994). Irradiated splenocytes were pulsed with decreasing concentrations of the lipids and control compounds, and incubated with DN32.D3 cells for 24 hours. Supernatants were harvested and IL-2 release was measured using a [$^3$H]-thymidine incorporation assay with an IL-2 dependent cell line as described by Cantu, et al., J. Immunol. 170:4673-4682 (2003).

Figure 4:
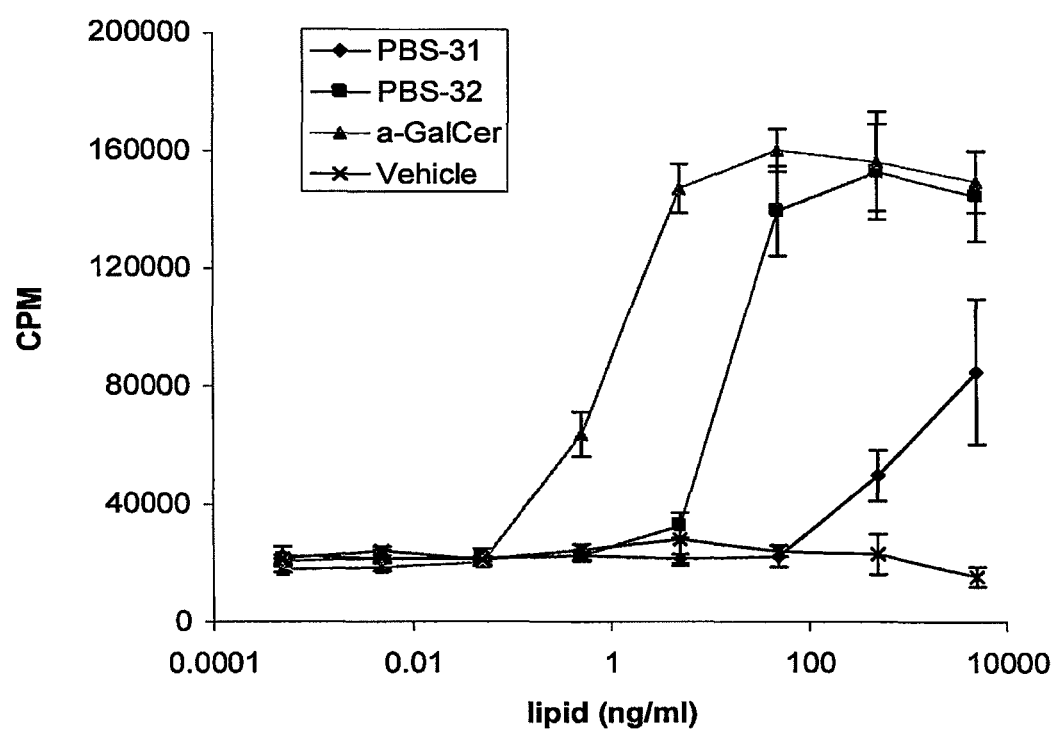
FIG. 4 is a graph showing differential activation and dose responsiveness of Vα14 NKT cell hybridoma DN32.D3 by PBS-32, PBS-31, αGalCer and vehicle.

As shown in FIG. 4, splenocytes efficiently presented PBS-31 and PBS-32, and produced a typical dose response curve. Similar results were obtained when mature DCs were used as the APCs (data not shown). DCs isolated from CD1-TD mice having a disruption of the cytoplasmic tail of CD1d were inefficient at presenting both PBS-31 and PBS-32 (data not shown). Therefore, presentation of PBS-31 and PBS-32 and concomitant stimulation of NKT cells is dependent on lysosomal targeting of CD1d.

To determine whether presentation of PBS-31 and PBS-32 to NKT cells was dependent on processing by DCs, a DC-free assay was used in which murine CD1d was coated on 96 well plates. PBS-31, PBS-32 and control compounds were added at various concentrations in the presence and absence of saposin B. DN32.D3 cells were added and supernatants were harvested after 24 hours and production of IL-2 was measured. The assay confirmed that saposin B is required for loading and further demonstrated that: 1) stimulation of NKT cells by PBS-31 and PBS-32 does not require processing by DCs; and 2) ceramide PBS-32 was consistently more potent than phytoceramide PBS-31 (data not shown).

Example 4

Cytokine Production by PBS-31 and PBS-32 Stimulated NKT Cells

Figure 5:
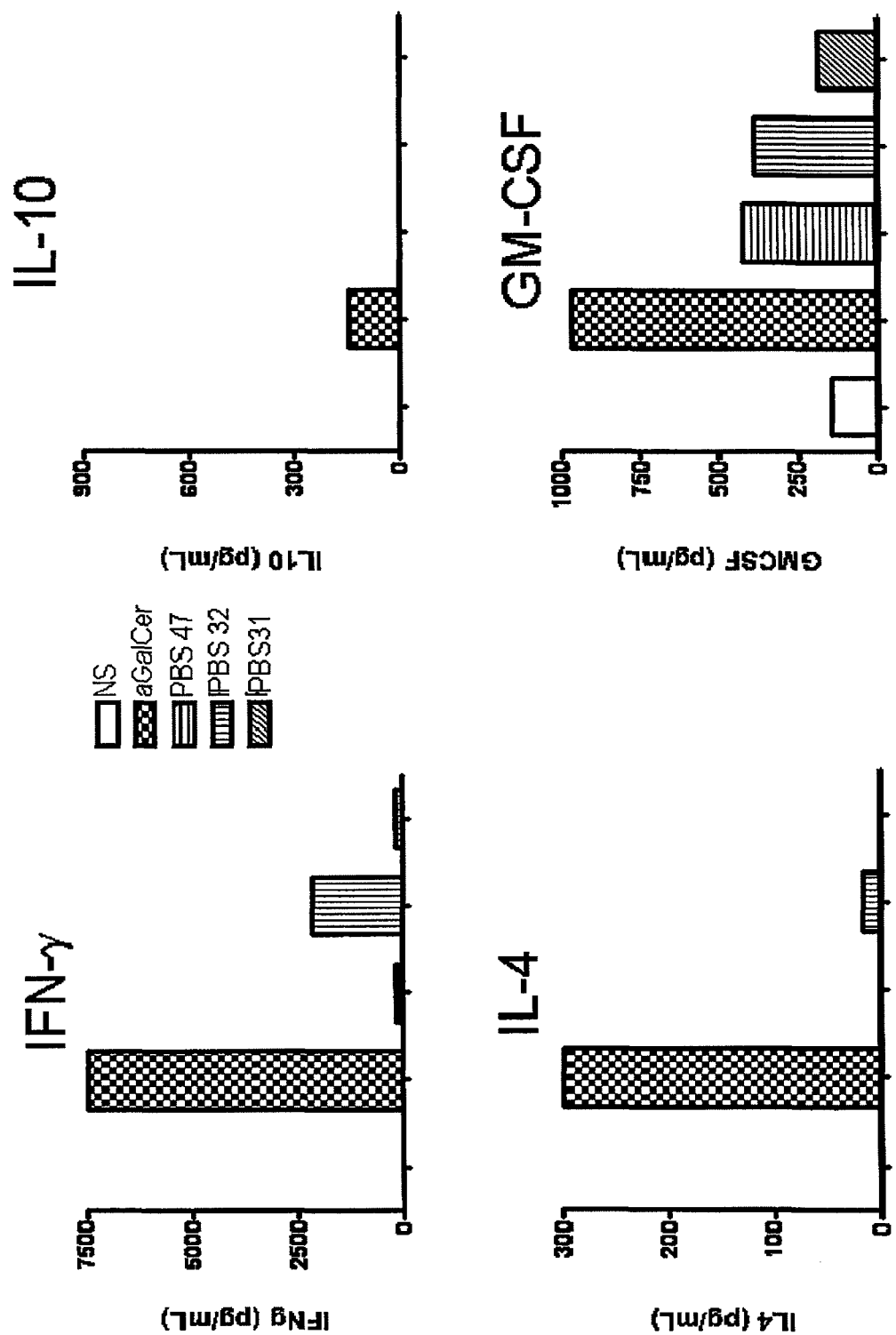
FIG. 5 is a graph showing results of enzyme-linked immunosorbant assays (ELISAs) measuring IFN-γ, IL-10, IL-4 and GM-CSF production following 24 hour stimulation of splenocytes with PBS-47, PBS-32, PBS-31 and αGalCer.

NKT cells were stimulated with PBS-32 or control compounds presented by plate-bound CD1d, splenocytes or purified mature DCs. Production of IFN-γ, IL-4, IL-10 and GM-CSF was measured by ELISA. As shown in FIG. 5, following 24 hours incubation with splenocytes, PBS-32 induced secretion of IFN-γ, IL-4 and GM-CSF, but not IL-10 and PBS-31 induced only GM-CSF. The control lipids (glucosyl and galactosyl) were negative in the same assays. Cytokine induction was CD1d-dependent because induction was blocked by anti-CD1d antibodies and no cytokine induction was observed when DCs from CD1d$^{-/-}$ mice were used (data not shown).

In vivo, following intravenous injection of 1 μg of positive control compound, αGalCer, or PBS-32, IFN-γ production in the serum of C57Bl/6 mice was measured by ELISA and was very similar for both compounds (2500 pg/ml and 1500 pg/ml at 24 hours, respectively). IL-4 was undetectable following PBS-32 injection. Also, PBS-32 induced earlier IFN-γ production than α-GalCer. At eight hours post-injection, PBS-32 induced 600 pg/ml IFN-γ.

Example 5

PBS-32-CD1d Tetramer Binding to Vα14 NKT Cells

PBS-32-loaded CD1d tetramers, as well as control αGalCer tetramers, were prepared as described in Benlagha et al., J. Exp. Med. 191: 1895-1903 (2000) incorporated herein by reference in its entirety. The resulting tetramers were used to stain a murine Vα14 NKT cell line. After washing, the cells were analyzed on a FACSCalibur (BD Biosciences) using FlowJo software. PBS-32-CD1d tetramer staining was less intense than for CD1d-αGalCer tetramers but homogenous, indicating that most canonical NKT cells were stained by this reagent (data not shown).

Figure 6:
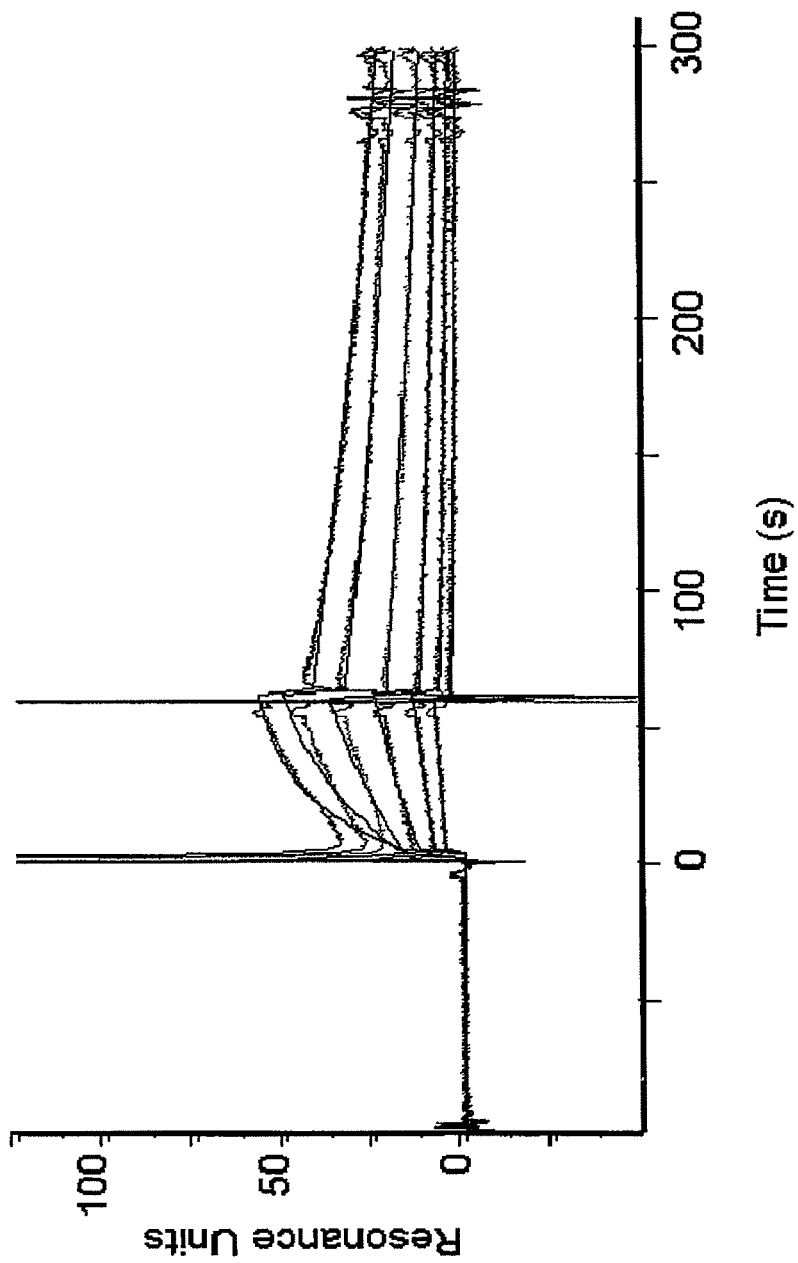
FIG. 6 is a graph showing the results of surface plasmon resonance (SPR) measurements of the binding of PBS-32-CD1d complexes to recombinant Vα14/2Cβ TCR.

The affinity of CD1d-PBS-32 complexes for Vα14/2Cβ T cell receptors (TCRs) was directly measured at 25° C. by SPR on a BIAcore 2000 instrument. The TCR was immobilized on a sensor chip and CD1d-PBS-32 complexes were injected at 10, 5, 2.5, 1.25, 0.625, 0.3125 μM in PBS buffer. In all experiments, empty CD1d at the same concentration (10, 5, 2.5, 1.25, 0.625, 0.3125 μM) was used as a negative control and subtracted from the corresponding experimental group. On- and off-rates were obtained by non-linear curve fitting using the 1:1 Langmuir binding model and BIAevaluation 3000 software. Chi$^2$ was 0.48. As shown in FIG. 6, CD1d-PBS-32 complex affinity for the Vα14/2CβTCR was found to be 0.3 mM. As previously reported, this TCR has an affinity of 30 nM for control CD1d-αGalCer. Cantu et al., J. Immunol. 170: 4673-82 (2003), incorporated herein by reference in its entirety.

Example 6

Activation of Human NKT Cells

Figure 7:
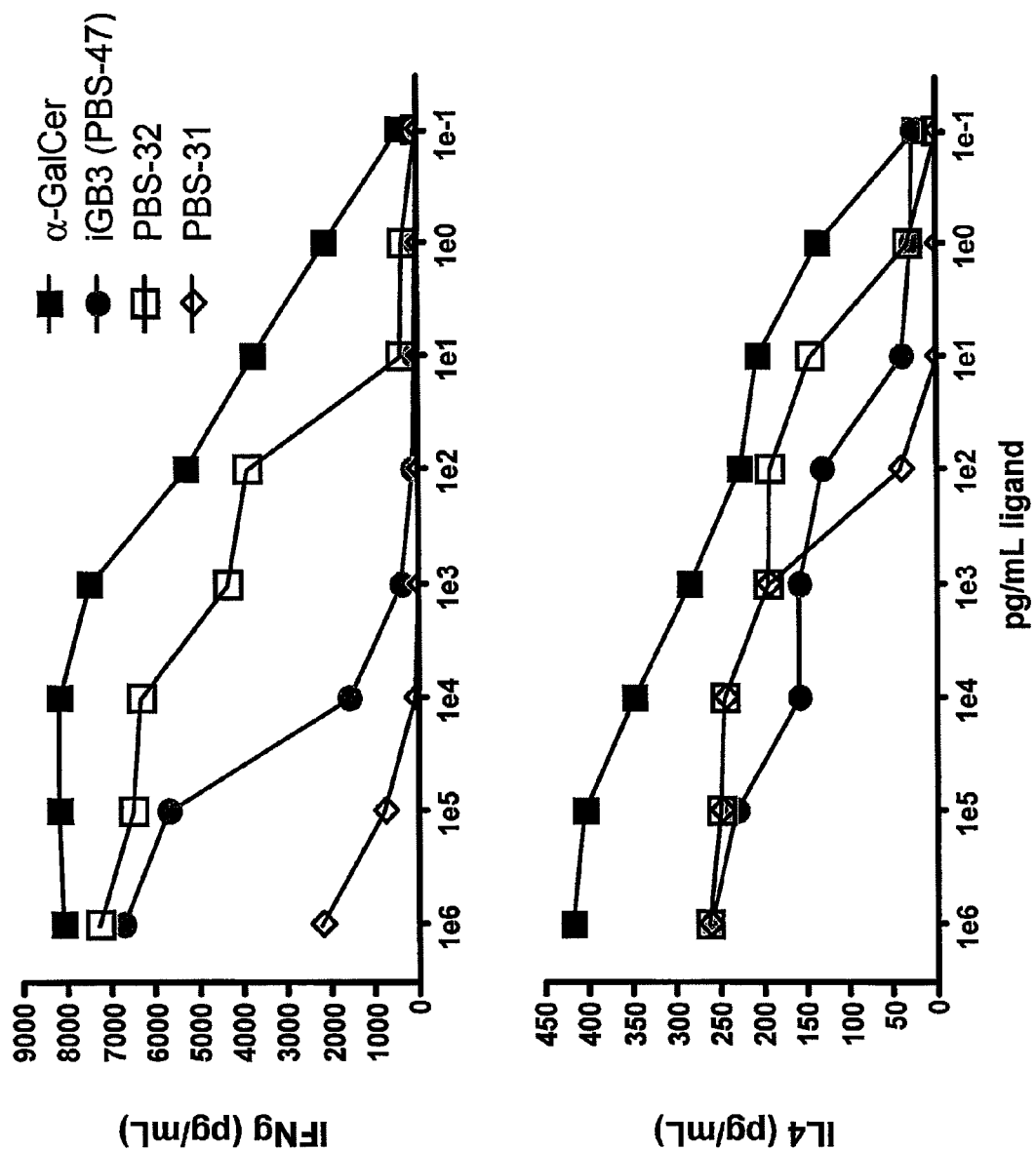
FIG. 7 is a graph showing activation of a human NKT cell line by homologous DCs pulsed with decreasing concentrations of αGalCer, PBS-47, PBS-32 and PBS-31. Activation of NKT cells was measured by ELISA for IFN-γ and IL-4.

The agonistic activity of PBS-31 and PBS-32 was examined for human NKT cells. A human NKT cell line was stimulated with irradiated peripheral blood lymphocytes (PBLs) or in vitro matured DCs in the presence of PBS-31, PBS-32 and control lipid, iGB3. (Mattner et al., Nature 434: 525-529 (2005) incorporated herein by reference in its entirety.) After 24 hours incubation, supernatants were harvested and assayed for the presence of IL-4 and IFN-γ by ELISA. As shown in FIG. 7, PBS-32 was able to induce IFN-γ and IL-4 secretion. PBS-32, PBS-31 and iGB3 induced almost equivalent amounts of IL-4, but PBS-31 induced significantly less IFN-γ.

Example 7

Induction of DC Maturation In Vivo

Mice were injected with α-GalCer, PBS-31 and PBS-32 and DC differentiation was examined in splenic DCs by analyzing cell surface marker expression.

Three mice in each group were injected intravenously with 1 µg lipid or vehicle alone. At 24 hours post-injection, CD1d expression was examined on splenic B cells (B220+), macrophages (CD11b+) and DCs (CD11c+) by FACS analysis using a FACScalibur machine and FlowJo analysis software.

In each animal, CD1d expression was increased on macrophages when compared to the mean fluorescence intensity of the control group (MFI going from —20 to 200). No differences in CD1d expression were observed on any other cell subset examined.

Figure 8:
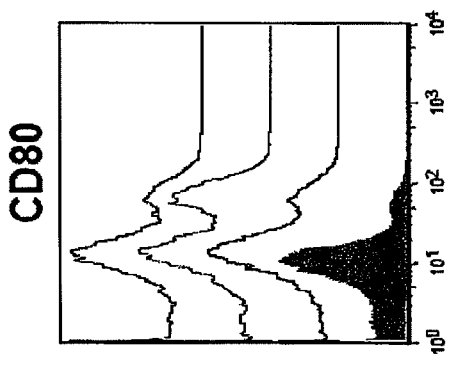
FIG. 8 is a graph showing results of fluorescence activated cell sorting (FACS) analysis for cell surface expression of CD40, CD80, CD86 and MHC class II by splenic DCs (CD11c+, CD8a+ and CD11c+/CD8a−) 24 hours after injection with PBS-31, PBS-32, αGalCer and vehicle.
Figure 8:
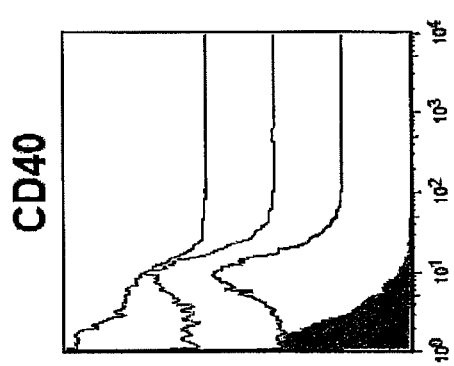
Figure 8:
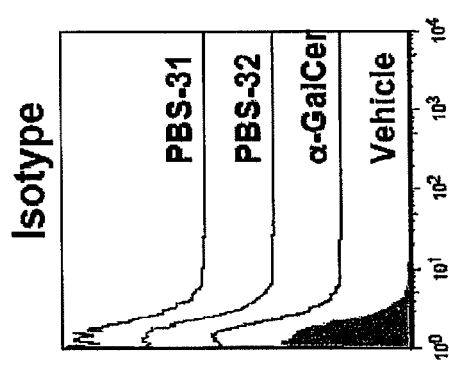
Figure 8:
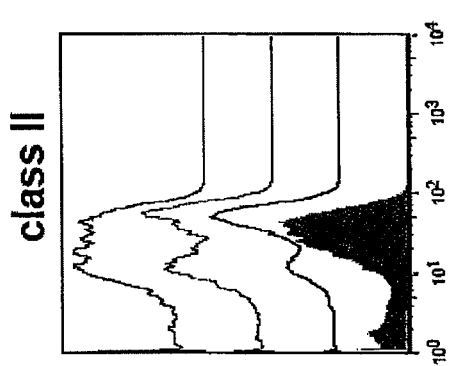
Figure 8:
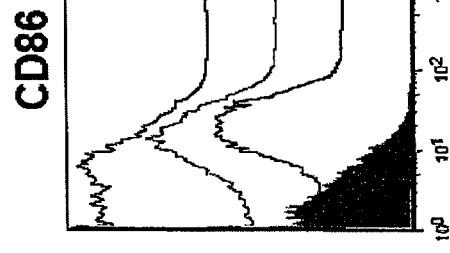

The maturation of DCs was analyzed by measuring expression of CD40, CD80, CD86, and MHC class II on CD11c$^+$/CD8$^+$ and CD11c$^+$/CD8$^-$ cells (FIG. 8). Both subsets of DCs demonstrated a mature phenotype as determined by cell surface marker expression after injection of PBS-32, PBS-31 or αGalCer. Profiles of maturation were similar for PBS-32 and αGalCer. Similar to the results obtained in the NKT cell activation assays, PBS-31 had a less pronounced effect than did PBS-32 or αGalCer. This lesser potency of PBS-31 could not be overcome by increasing the doses up to 50 µg per mouse (data not shown). PBS-32 and αGalCer reached maximal induction between 0.1 and 1 µg (data not shown).

Induction of DC maturation was unaffected in MyD88$^{-/-}$ and MyD88$^{-/-}$TRIF$^{-/-}$ knock out animals in which the Toll-like receptor pathway is partially, or totally impaired, respectively (data not shown). The CD1d-dependence was confirmed by injecting CD1d$^{-/-}$ mice with the lipids. As predicted, DC maturation did not occur in CD1d$^{-/-}$ mice after injection with the lipids.

Example 8

Adjuvant Capability Analysis

The potential adjuvanticity of PBS-31 and PBS-32 combined with a nominal protein antigen, ovalbumin, was conducted following a protocol similar to that of Fujii et al., J. Exp. Med. 198: 267-279 (2003) and Hermans et al., J. Immunol. 171: 5140-5147 (2003), which are incorporated herein by reference in their entireties. Ovalbumin was injected intravenously either alone or in combination with 1 µg of PBS-31, PBS-32 or PBS-57. FIG. 9 demonstrates results from a representative experiment. In the absence of working tetramers to follow MHC class II responses, only CD8+ responses and B cell responses were evaluated.

Figure 9A:
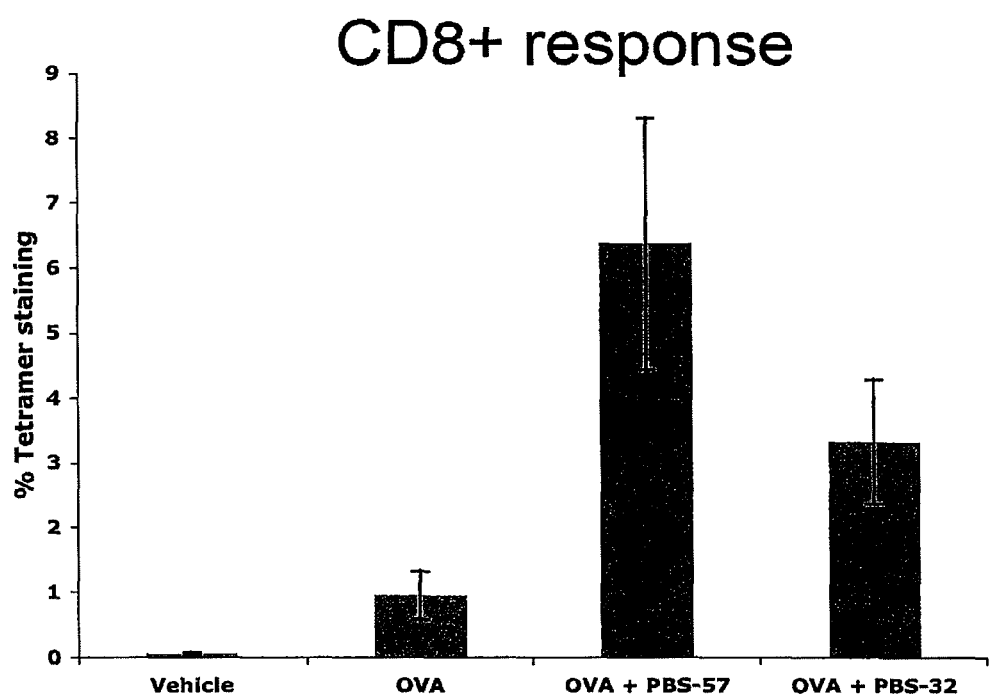
FIG. 9A shows percentages of H-2K$^b$/ova$_{257-264}$ responsive CD8+ T-cells (as indicated by tetramer staining and FACS analysis) after administration of vehicle alone, OVA alone, OVA+PBS-57 and OVA+PBS-32.
Figure 9B:
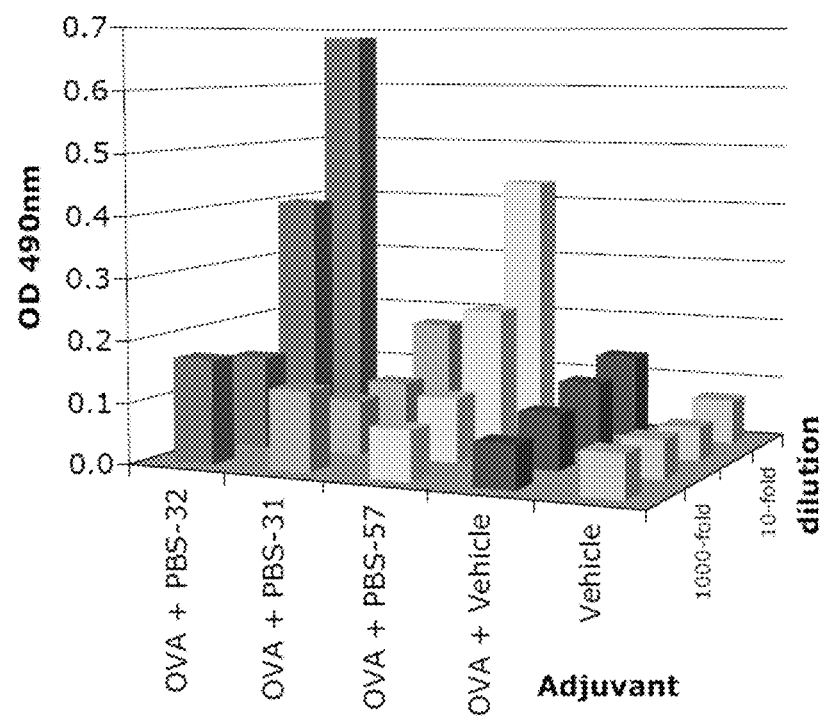
FIG. 9B shows relative amounts of anti-ovalbumin IgG antibody, as measured by ELISA.

CD8+ T cell responses were evaluated by enumerating the H-2K$^b$/ova$_{257-264}$ tetramer positive cells in peripheral blood at 7 days post-injection and are expressed as the percentage H-2K$^b$/ova$_{257-264}$ positive cells in the CD8+ T cell pool. At day 7 post-injection, antigen-specific H-2K$^b$/ova$_{257-264}$ tetramer positive cells were increased to about 3% in the PBS-32 injected group whereas they expanded to almost 6% in the PBS-57 treated group (FIG. 9A). In both groups, the IgG anti-ovalbumin response was dramatically boosted in a dose-dependent manner when compared to the control group as measured by ELISA using an anti-IgG specific secondary antibody (FIG. 9B). These strong IgG responses may indirectly reflect a significant boost of the ovalbumin-specific CD4+T helper compartment as well.

When CD1d$^{-/-}$ mice were injected following the same protocol, no increase in either anti-ovalbumin IgG or in the anti-ovalbumin CD8+ T cells were noted (data not shown). These results confirmed that PBS-32 had adjuvant activity when used in combination with a purified protein antigen.

Example 9

PBS-32 Recruits T-Cells in an LCMV Model

The ability to use NKT cell/DC cooperation to stimulate adaptive immunity was further tested in a model infection system, the lymphocytic choriomeningitis virus (LCMV) infection of mice. The natural host of LCMV is the mouse and both anti-viral MHC class I-restricted and MHC class II-restricted T cell responses have been finely mapped. Seven epitopes are identified for the nucleoprotein (NP) and glycoprotein (GP) on H-2K$^b$ (NP$_{205-212}$, GP$_{34-43}$, GP$_{118-125}$) and H-2 D$^b$ (NP$_{396-404}$, GP$_{33-41}$, GP$_{92-101}$, GP$_{276-286}$) and two epitopes are restricted on I-A$^b$ (GP$_{61-80}$, NP$_{309-328}$).

Figure 10:
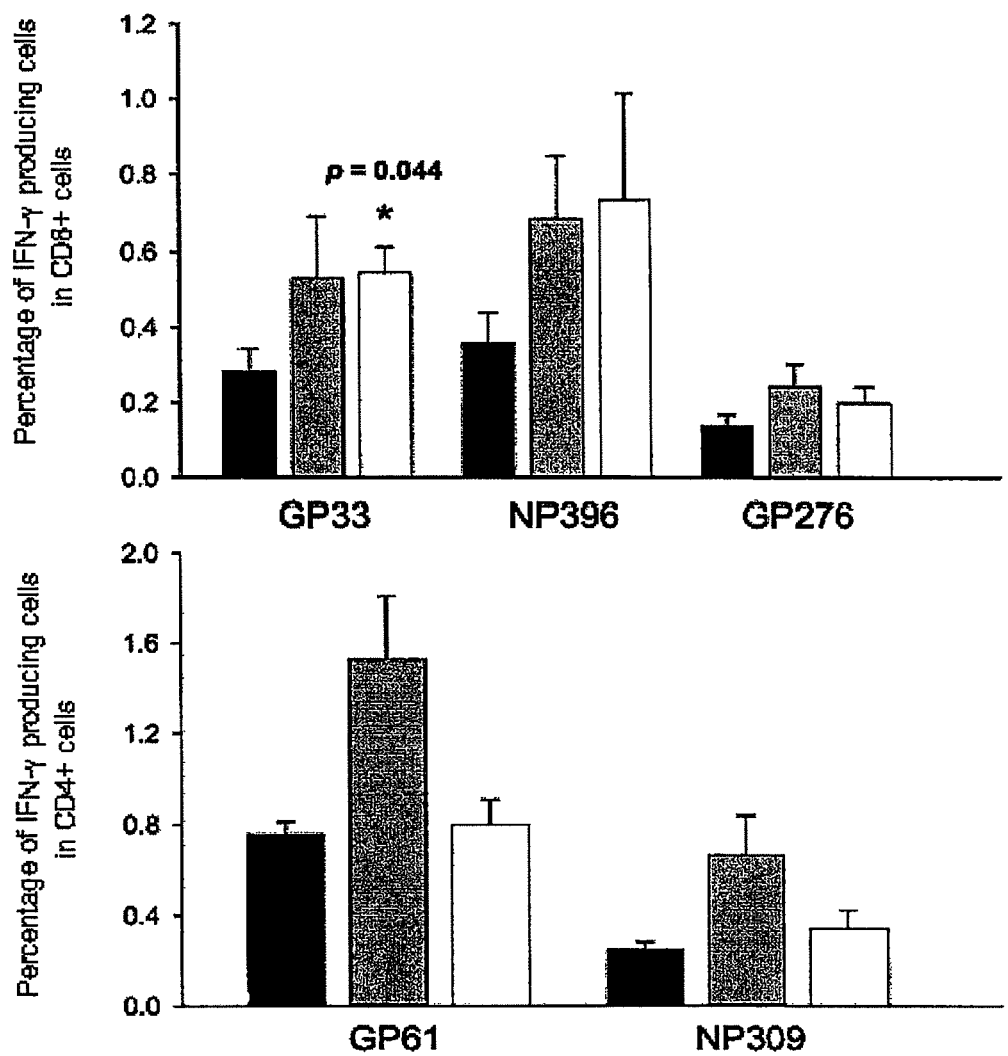
FIG. 10 is a graph showing results of FACS staining for IFN-γ-producing CD8+ and CD4+ T-cells after a five hour in vitro pulse with LCMV antigens and antigen presenting cells.
Figure 11A:
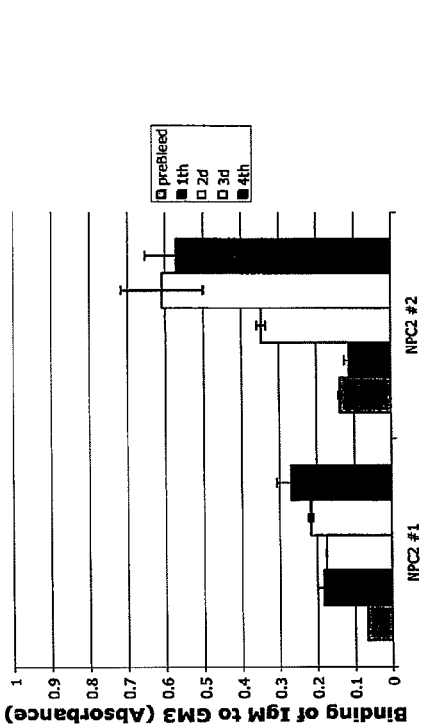
FIG. 11A is a graph of antibody concentrations using of hGM2a and mNPC2.
Figure 11A:
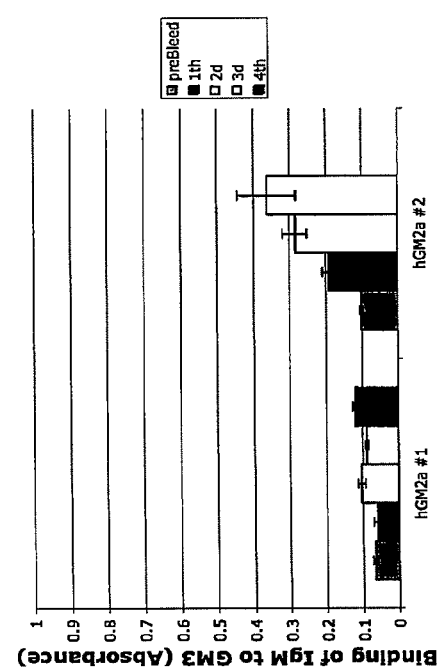
Figure 11A:
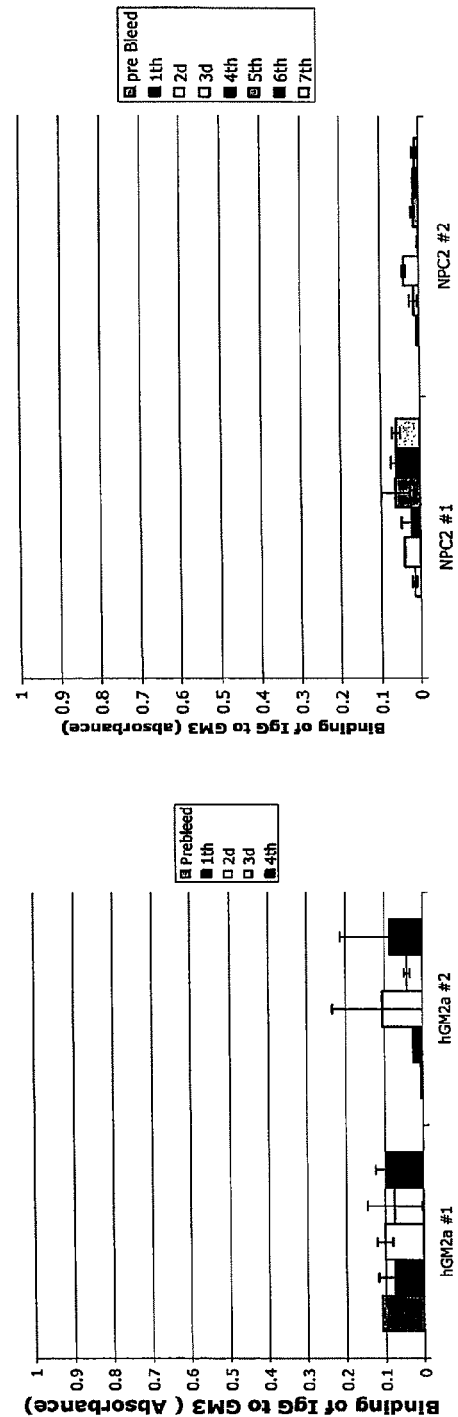
Figure 11B:
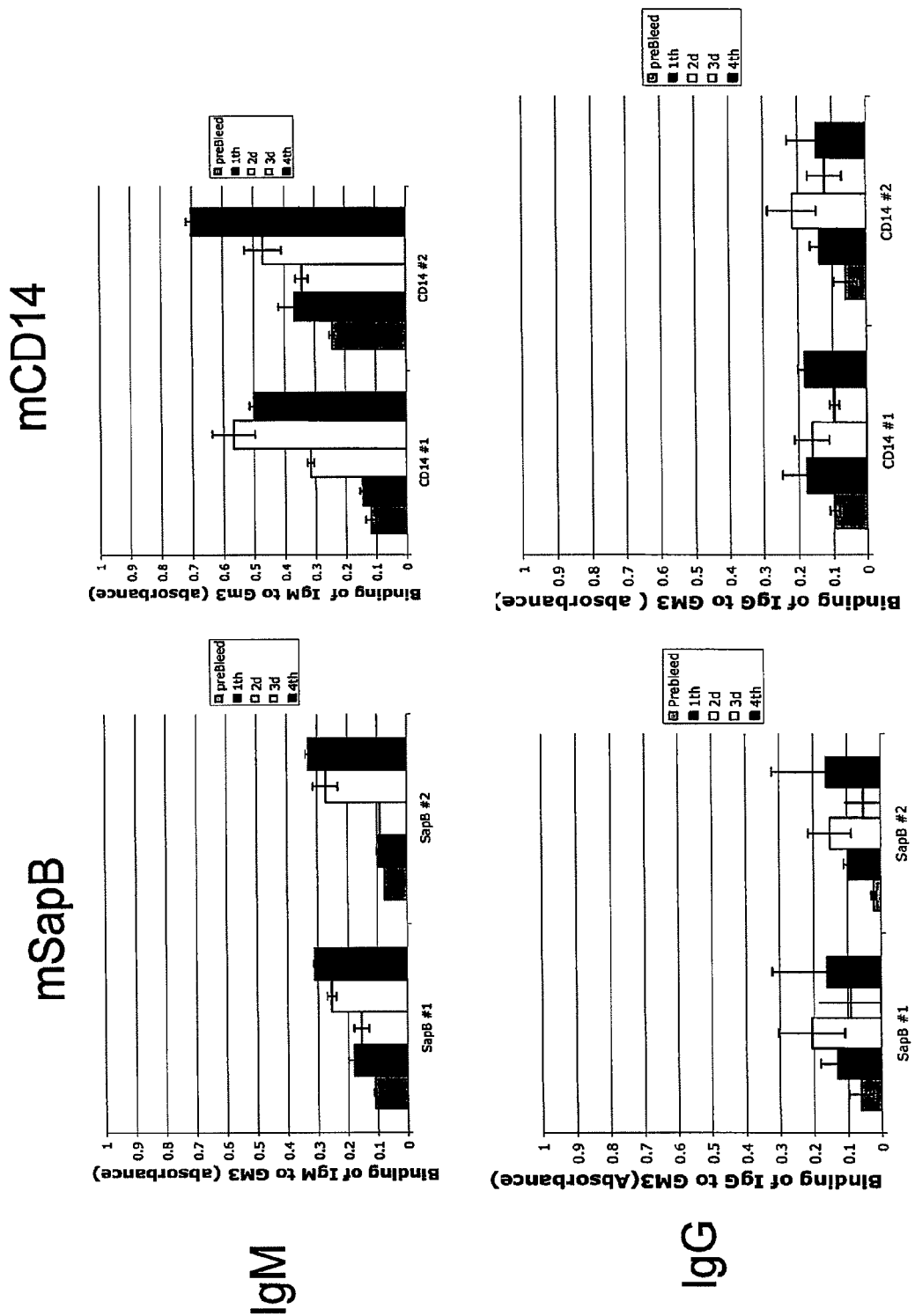
FIG. 11B is the graph of antibody concentrations using mSapB and mCD14.
Figure 11C:
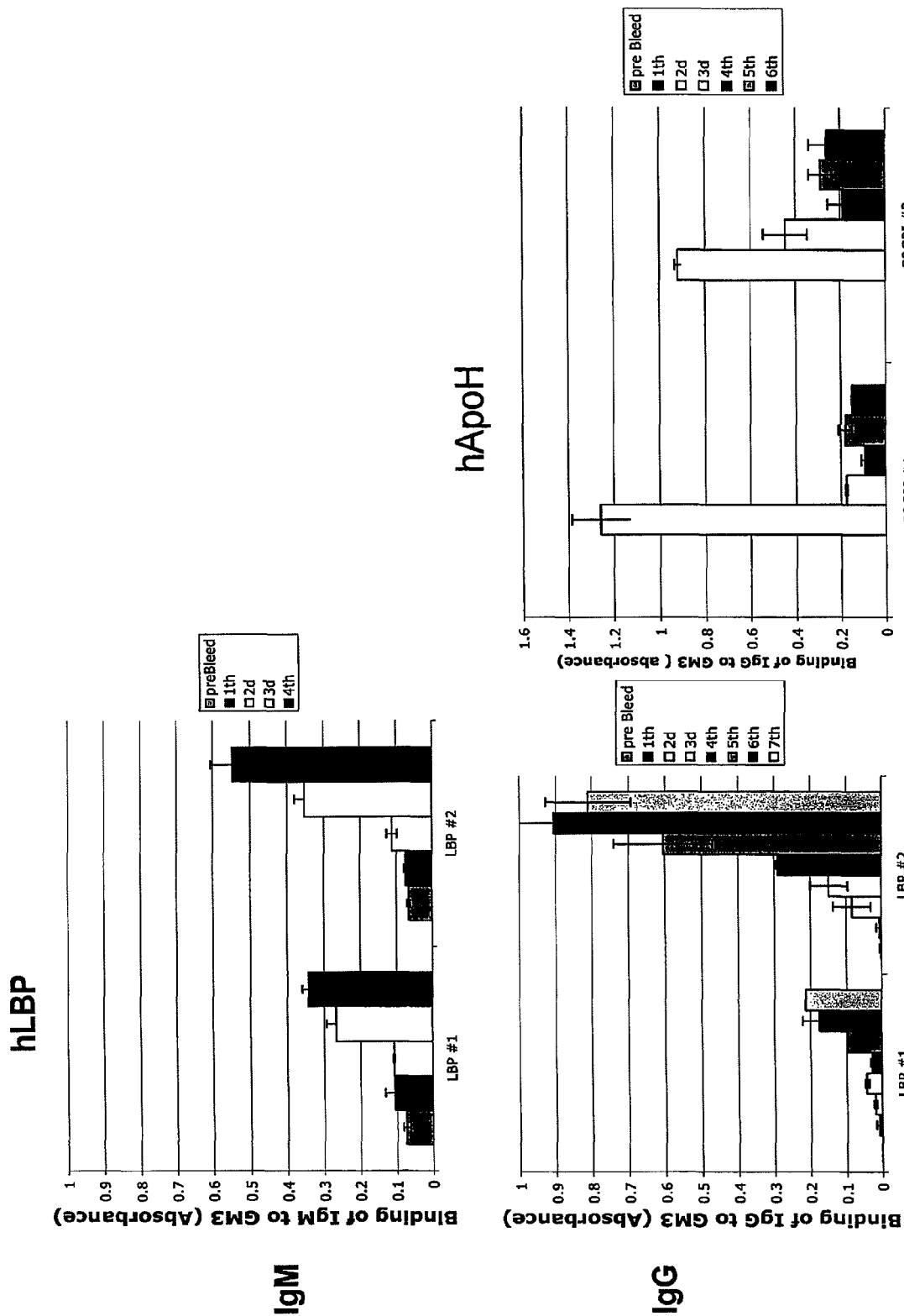
FIG. 11C is the graph of antibody concentrations using hLBP and hApoH.
Figure 12:
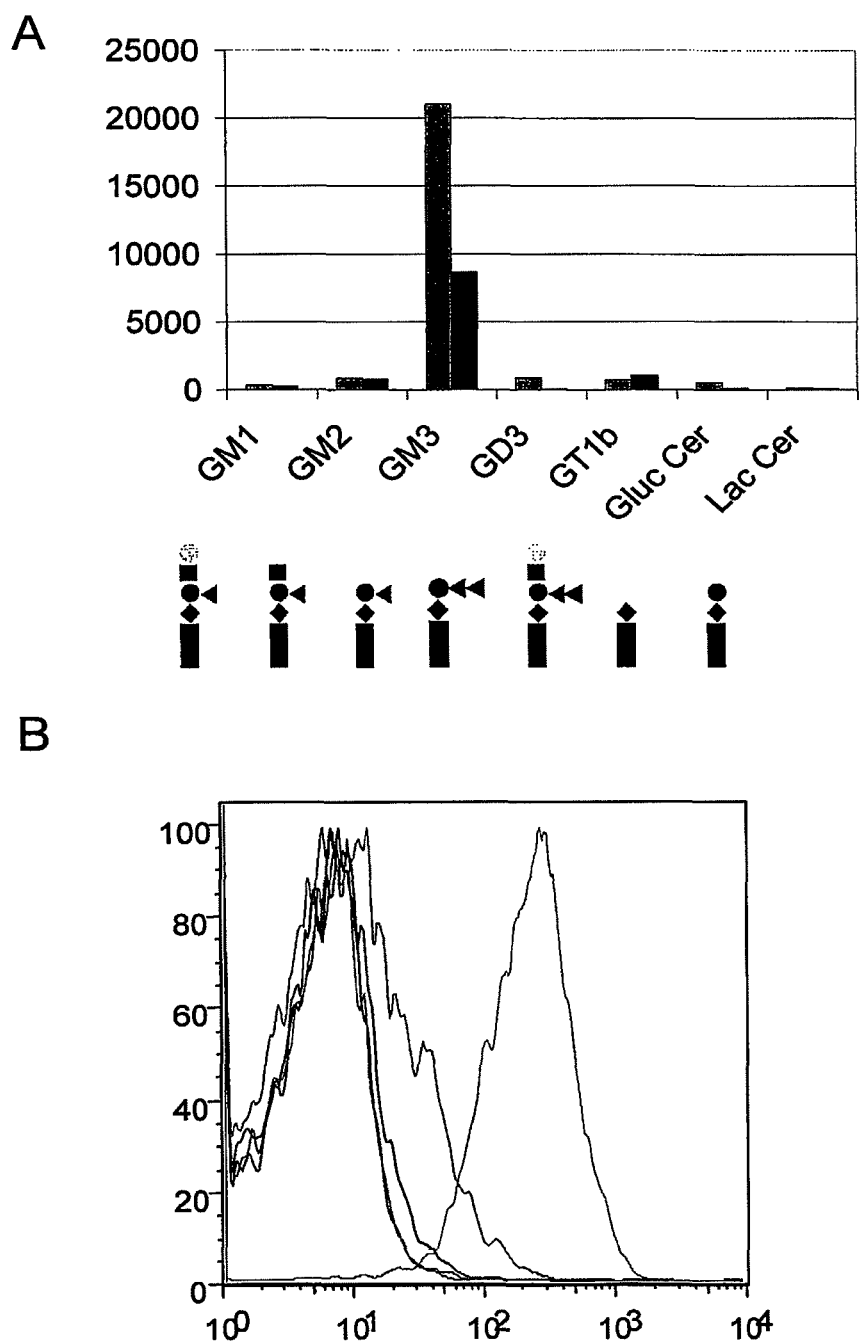
FIG. 12 is a graph showing specificity of anti-GM3 monoclonal antibodies produced by mice immunized with lipids as measured by ELISA and FACS analysis of liposome-coated glass beads.

To evaluate if the injection of PBS-32 or control αGalCer could change the dynamics of the anti-LCMV T cell response, C57Bl/6 mice were injected intravenously with 1 µg of PBS-32, αGalCer or vehicle before being inoculated intraperitoneally with 10$^6$ PFU of infectious LCMV$_{Arm}$. At day 8 post-infection, the frequency of CD8+ T cells specific for GP$_{33}$, NP$_{396}$ and GP$_{276}$, and the frequency of CD4+ T cells specific for GP$_{61}$ and NP$_{309}$, was determined by intracellular FACS staining for IFN-γ after a five hour in vitro pulse with peptide and APC. As seen in FIG. 10, LCMV alone induced a strong anti-LCMV class I and class II restricted response against all tested epitopes (black bars). However, despite this strong basal response, α-GalCer was able to significantly increase the CD8+ response (white bars), and PBS-32 did equally well (grey bars). More surprisingly, whereas the CD4+ response was unchanged by the injection of α-GalCer, PBS-32 was able to induce a significant increase of both anti-GP$_{61}$ and anti-NP$_{309}$ I-A$^b$-restricted responses. Therefore, in contrast to the results obtained with a protein antigen, αGalCer and PBS-32 have different abilities to recruit CD4+ and CD8+ T cells in this viral infection model.

Example 10

PBS-32 Enhances Vaccination Against Infection with a Pathogenic Microorganism The ability of NKT cell agonist compounds to stimulate a memory immune response and vaccinate against infection with a pathogenic microorganism will be tested in a mouse infection model. Mice will be injected intraperitoneally or intravenously with one of the following: a composition comprising PBS-32 and an infectious agent antigen such as lipoarabinomannan from *Mycobacterium tuberculosis* in a physiologically acceptable vehicle; the antigen alone in a physiologically acceptable vehicle; or the vehicle alone. At least one week after immunization, the immune response will be assessed by harvesting the spleen, stimulating the recovered cells in vitro with the antigen and performing ELISA and FACS analysis to assess cytokine induction, expression of activation-related cell surface markers and antibody production on various immune cell types including NKT cells, CD4+ T cells, CD8+ T cells, APCs and B cells.

A second set of immunized animals will be experimentally infected with decreasing doses of the infectious agent to produce a dose response curve and determine the LD$_{50}$ (amount of infectious agent required to kill 50% of the animals) and $ID_{50}$ (amount of infectious agent required to establish an infection). The animals will be scored on a scale of 1 to 5 for disease symptom severity (1 being no disease symptoms and 5 representing dead or euthanized animals). The animals will be scored on a daily basis after challenge to assess whether the immunization reduced disease severity. Sample tissues will be harvested at various time points over the course of the infection and assayed for the presence of the infectious agent by methods known to those of skill in the art. The results will demonstrate that when the immunization procedure included PBS-32 as an adjuvant, the immune response to the antigen is enhanced, the $LD_{50}$ is higher and the $ID_{50}$ is higher (i.e., more microorganisms are needed to kill or establish an infection in the animal).

The invention has been described with reference to various specific embodiments and techniques. However, it should be understood that many variations and modifications may be made while remaining within the spirit and scope of the invention.

We claim:

1. A method of enhancing an immune response in a subject comprising administering to the subject a composition comprising a compound of formula (I)

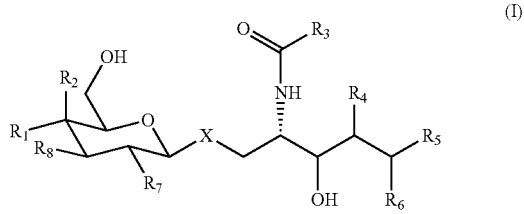

wherein:
X is —O—;
$R_1$ is —OH;
$R_2$ is —H;
$R_3$ is a saturated or unsaturated hydrocarbon group having from about 7 to about 25 carbon atoms;
$R_5$ is a saturated or unsaturated hydrocarbon group having from about 5 to about 15 carbon atoms,
$R_6$ together with $R_4$ forms a carbon-carbon double bond;
$R_7$ is —OH; and
$R_8$ is —OSO$_3$H, —SO$_3$H, —PO$_4$, —PO$_4$H, or —COOH; and a physiologically acceptable vehicle.

2. The method of claim 1, wherein the immune response comprises the production of antibodies or comprises a helper, cytolytic or memory response.

3. The method of claim 1, wherein $R_8$ is —OSO$_3$H.

4. The method of claim 3, wherein $R_3$ is $C_{25}H_{51}$ and $R_5$ is $C_{13}H_{27}$.

5. The method of claim 1, wherein $R_3$ is $C_{25}H_{51}$ and $R_5$ is $C_{13}H_{27}$.

6. The method of claim 1, wherein the composition comprises an antigen.

7. The method of claim 6, wherein the composition is a vaccine.

8. The method of claim 6, wherein the antigen is a tumor antigen.

9. The method of claim 6, wherein the antigen is a bacterial or viral antigen.

10. A method of stimulating an NKT cell comprising contacting the NKT cell with a composition comprising a compound having a structural formula represented by (I):

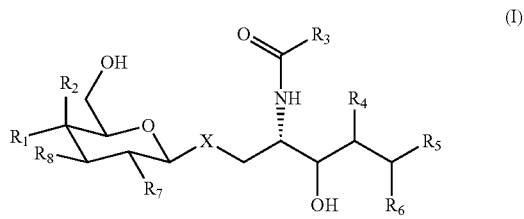

wherein:
X is —O—;
$R_1$ is —OH;
$R_2$, is —H;
$R_3$ is a saturated or unsaturated hydrocarbon group having from about 7 to about 25 carbon atoms;
$R_5$ is a saturated or unsaturated hydrocarbon group having from about 5 to about 15 carbon atoms,
$R_6$ together with $R_4$ forms a C—C double bond; and
$R_7$ is —OH; and
$R_8$ is —OSO$_3$H, —SO$_3$H, —PO$_4$, —PO$_4$H, or —COOH.

11. The method of claim 10, further comprising contacting the NKT cell with the composition in the presence of a CD1d monomer or tetramer.

12. The method of claim 11, wherein the compound is bound to the CD1d monomer or tetramer.

13. The method of claim 11, wherein the CD1d monomer or tetramer is soluble.

14. The method of claim 11, wherein the CD1d monomer is expressed on a cell surface.

15. The method of claim 14, wherein the cell is an antigen presenting cell.

16. The method of claim 10, wherein the NKT cell is cultured in vitro.

17. The method of claim 10, wherein the NKT cell is in a subject.

18. The method of claim 10, wherein $R_8$ is —OSO$_3$H.

19. The method of claim 18, wherein $R_3$ is $C_{25}H_{51}$ and $R_5$ is $C_{13}H_{27}$.

20. The method of claim 10, wherein $R_3$ is $C_{25}H_{51}$ and $R_5$ is $C_{13}H_{27}$.

21. The method of claim 10, wherein the composition comprises an antigen.

22. The method of claim 21, wherein the composition is a vaccine.

23. The method of claim 21, wherein the antigen is a tumor antigen.

24. The method of claim 21, wherein the antigen is a bacterial or viral antigen.

* * * * *